United States Patent
Zhou et al.

(10) Patent No.: US 11,328,185 B2
(45) Date of Patent: May 10, 2022

(54) NONINVASIVE, LABEL-FREE, IN VIVO FLOW CYTOMETRY USING SPECKLE CORRELATION TECHNIQUE

(71) Applicant: California Institute of Technology, Pasadena, CA (US)

(72) Inventors: Edward H. Zhou, Cupertino, CA (US); Michelle Cua, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 965 days.

(21) Appl. No.: 16/025,864

(22) Filed: Jul. 2, 2018

(65) Prior Publication Data

US 2019/0005351 A1     Jan. 3, 2019

Related U.S. Application Data

(60) Provisional application No. 62/527,237, filed on Jun. 30, 2017.

(51) Int. Cl.
    *G06K 9/62*          (2006.01)
    *G01N 15/14*        (2006.01)
          (Continued)

(52) U.S. Cl.
    CPC .............. *G06K 9/628* (2013.01); *A61B 5/1455* (2013.01); *A61B 5/14535* (2013.01);
                 (Continued)

(58) Field of Classification Search
    CPC .. G06K 9/628; G06K 9/00127; G06K 9/2027; A61B 90/20; A61B 5/14535; A61B 5/1455; G06T 7/254; G06T 7/246; G06T 7/0012; G06T 2207/10016; G06T 2207/30024; G06T 2207/30096; G06T 2207/30101; G06T 2207/30242; G06T 2207/30104; G01N 15/1404;
                 (Continued)

(56) References Cited

U.S. PATENT DOCUMENTS

| | | | | |
|---|---|---|---|---|
| 2002/0093641 A1* | 7/2002 | Ortyn | ................... | G01N 15/147 356/28 |
| 2016/0317020 A1* | 11/2016 | Liu | ....................... | A61B 3/0025 |
| 2021/0321887 A1* | 10/2021 | Fukazawa | ............ | A61B 5/0261 |

OTHER PUBLICATIONS

Ntziachristos, V., "Going deeper than microscopy: the optical imaging frontier in biology", Nature Methods, Aug. 2010, pp. 603-614, vol. 7, No. 8.

(Continued)

*Primary Examiner* — Amelie R Davis
*Assistant Examiner* — Helene Bor
(74) *Attorney, Agent, or Firm* — Gates & Cooper LLP

(57) ABSTRACT

A system and method for performing speckle correlation flow cytometry (SCFC). By subtracting out the stationary background when shining light through a sample (e.g., a vessel within a biological tissue), light only scattered by the desired targets (e.g., cells) can be captured and different types of targets (e.g., cells) can be distinguished by the autocorrelation of the speckle pattern. In this way, the targets (e.g., cells) can be classified and counted based on the features of their speckle correlations. The technique can be applied not only for noninvasive, label-free, in vivo CTC counting but also for counting other types of blood cells such as white blood cells or red blood cells.

19 Claims, 12 Drawing Sheets

(51) Int. Cl.
| | |
|---|---|
| *A61B 5/1455* | (2006.01) |
| *A61B 5/145* | (2006.01) |
| *G06T 7/00* | (2017.01) |
| *G06T 7/246* | (2017.01) |
| *A61B 90/20* | (2016.01) |
| *G06K 9/20* | (2006.01) |
| *G06K 9/00* | (2006.01) |
| *G06T 7/254* | (2017.01) |
| *G01N 15/10* | (2006.01) |

(52) U.S. Cl.
CPC ......... *A61B 90/20* (2016.02); *G01N 15/1404* (2013.01); *G01N 15/1429* (2013.01); *G01N 15/1459* (2013.01); *G06K 9/00127* (2013.01); *G06K 9/2027* (2013.01); *G06T 7/0012* (2013.01); *G06T 7/246* (2017.01); *G06T 7/254* (2017.01); *G01N 2015/1006* (2013.01); *G01N 2015/1454* (2013.01); *G06T 2207/10016* (2013.01); *G06T 2207/30024* (2013.01); *G06T 2207/30096* (2013.01); *G06T 2207/30101* (2013.01); *G06T 2207/30104* (2013.01); *G06T 2207/30242* (2013.01)

(58) Field of Classification Search
CPC ........... G01N 15/1429; G01N 15/1459; G01N 2015/1006; G01N 2015/1454
See application file for complete search history.

(56) References Cited

OTHER PUBLICATIONS

Huang, D., et al., "Optical coherence tomography", Science, Nov. 1991, pp. 1178-1181, vol. 254, No. 5035.
Andersson-Engels, S., et al., "Time-resolved transillumination for medical diagnostics", Optics Letters, Nov. 1990, pp. 1179-1181, vol. 15, No. 21.
Chapman, G.H., et al., "Angular Domain Imaging of Objects Within Highly Scattering Media Using Silicon Micromachined Collimating Arrays", IEEE Journal of Selected Topics in Quantum Electronics, Mar./Apr. 2003, pp. 257-266, vol. 9, No. 2.
Kang, S., et al., "Imaging deep within a scattering medium using collective accumulation of single-scattered waves", Nature Photonics, Apr. 2015, pp. 253-258, vol. 9.
Ramachandran, H., et al., "Two-dimensional imaging through turbid media using a continuous wave light source", Optics Communications, Sep. 1998, pp. 255-260, vol. 154.
Sudarsanam, S., et al., "Real-time imaging through strongly scattering media: seeing through turbid media, instantly", Scientific Reports, 2016, pp. 1-9, vol. 6, No. 25033.
Helmchen, F., et al., "Deep tissue two-photon microscopy", Nature Methods, Dec. 2005, pp. 932-940, vol. 2, No. 12.
Mosk, A.P., et al., "Controlling waves in space and time for imaging and focusing in complex media", Nature Photonics, May 2012, pp. 283-292, vol. 6.
Vellekoop, I.M., et al., "Focusing coherent light through opaque strongly scattering media", Optics Letters, Aug. 2007, pp. 2309-2311, vol. 32, No. 16.
Xu, X., et al., "Time-reversed ultrasonically encoded optical focusing into scattering media", Nature Photonics, Mar. 2011, pp. 154-157, vol. 5.
Wang, Y.M., "Deep-tissue focal fluorescence imaging with digitally time-reversed ultrasound-encoded light", Nature Communications, 2012, pp. 1-8, vol. 3, No. 928.
Bertolotti, J., et al., "Non-invasive imaging through opaque scattering layers", Nature, Nov. 2012, pp. 232-234, vol. 491.
Katz, O., et al., "Non-invasive single-shot imaging through scattering layers and around corners via speckle correlations", Nature Photonics, Oct. 2014, pp. 784-790, vol. 8.
Zhou, E.H., et al., "Focusing on moving targets through scattering samples", Optica, Oct. 2014, pp. 227-232 and Supplementary Material, vol. 1, No. 4.
Ma, C., et al., "Time-reversed adapted-perturbation (TRAP) optical focusing onto dynamic objects inside scattering media", Nature Photonics, Dec. 2014, pp. 931-936, vol. 8, No. 12.
Fienup, J.R., "Phase retrieval algorithms: a comparison", Applied Optics, Aug. 1982, pp. 2758-2769, vol. 21, No. 15.
Feng, S., et al., "Correlations and fluctuations of coherent wave transmission through disordered media", Physical Review Letters, Aug. 1988, pp. 834-837, vol. 61, No. 7.
Berkovits, R., et al., "Memory effect of waves in disordered systems: a real-space approach", Jul. 1989, pp. 737-740, vol. 40, No. 1.
Schott, S., et al., "Characterization of the angular memory effect of scattered light in biological tissues", Optics Express, May 2015, pp. 1-12, vol. 23, No. 10.
Fienup, J., et al., "Reconstruction of the support of an object from the support of its autocorrelation", J. Opt. Soc. Am, May 1982, pp. 610-624, vol. 72, No. 5.
Fienup, J., et al., "Phase-retrieval stagnation problems and solutions", J. Opt. Soc. Am. A, Nov. 1986, pp. 1897-1907, vol. 3, No. 11.
Ruffing, B., et al., "Spectral correlation of partially or fully developed speckle patterns generated by rough surfaces", J. Opt. Soc. Am. A, Oct. 1985, pp. 1637-1643, vol. 2, No. 10.
Katz, O., et al., "Looking around corners and through thin turbid layers in real time with scattered incoherent light", Nature Photonics, Aug. 2012, pp. 549-553, vol. 6.
Freund, I., "Looking Through Walls and Around Corners", Physica A, 1990, pp. 49-65, vol. 168.
Judkewitz, B., et al., "Translation correlations in anisotropically scattering media", Nature Physics, Aug. 2015, pp. 684-689, vol. 11.
Brake, J., et al., "Analyzing the relationship between decorrelation time and tissue thickness in acute rat brain slices using multispeckle diffusing wave spectroscopy", Journal of the Optical Society of America A, Feb. 2016, pp. 270-275, vol. 33, No. 2.
Li, H., et al., "Simulation and experimental verification for imaging of gray-scale objects through scattering layers", Applied Optics, Dec. 2016, pp. 9731-9737, vol. 55, No. 34.
Allard, J.W., et al., "Tumor Cells Circulate in the Peripheral Blood of All Major Carcinomas but not in Healthy Subjects or Patients With Nonmalignant Diseases", Clinical Cancer Research, Oct. 2004, pp. 6897-6904, vol. 10.
Cristofanilli, M., et al., "Circulating Tumor Cells: A Novel Prognostic Factor for Newly Diagnosed Metastatic Breast Cancer", Journal of Clinical Oncology, Mar. 2005, pp. 1420-1430, vol. 23, No. 7.
Golan, L., et al., "Noninvasive imaging of flowing blood cells using label-free spectrally encoded flow cytometry", Biomedical Optics Express, Jun. 2012, pp. 1455-1464, vol. 3, No. 6.
Kemmler, M., et al., "Noninvasive time-dependent cytometry monitoring by digital holography", Journal of Biomedical Optics, Nov./Dec. 2007, pp. 064002-1-064002-10, vol. 12, No. 6.
Galanzha, E.I., et al., "In vivo, Noninvasive, Label-Free Detection and Eradication of Circulating Metastatic Melanoma Cells Using Two-Color Photoacoustic Flow Cytometry with a Diode Laser", Cancer Research, Oct. 2009, pp. 7926-7934, vol. 69, No. 20.
Cua, M., et al., "Imaging moving targets through scattering media", Optics Express, Feb. 2017, pp. 3935-3945, vol. 25, No. 4.
Freund, I., et al., "Memory Effects in Propagation of Optical Waves through Disordered Media", Physical Review Letters, Nov. 1988, pp. 2328-2332, vol. 61, No. 20.
Osnabrugge, G., et al., "Generalized optical memory effect", Optica, Aug. 2017, pp. 886-892, vol. 4, No. 8.
"Highspeed Cameras for challenging applications", https://www.pco.de/highspeed-cameras/, as downloaded Mar. 20, 2020.

* cited by examiner

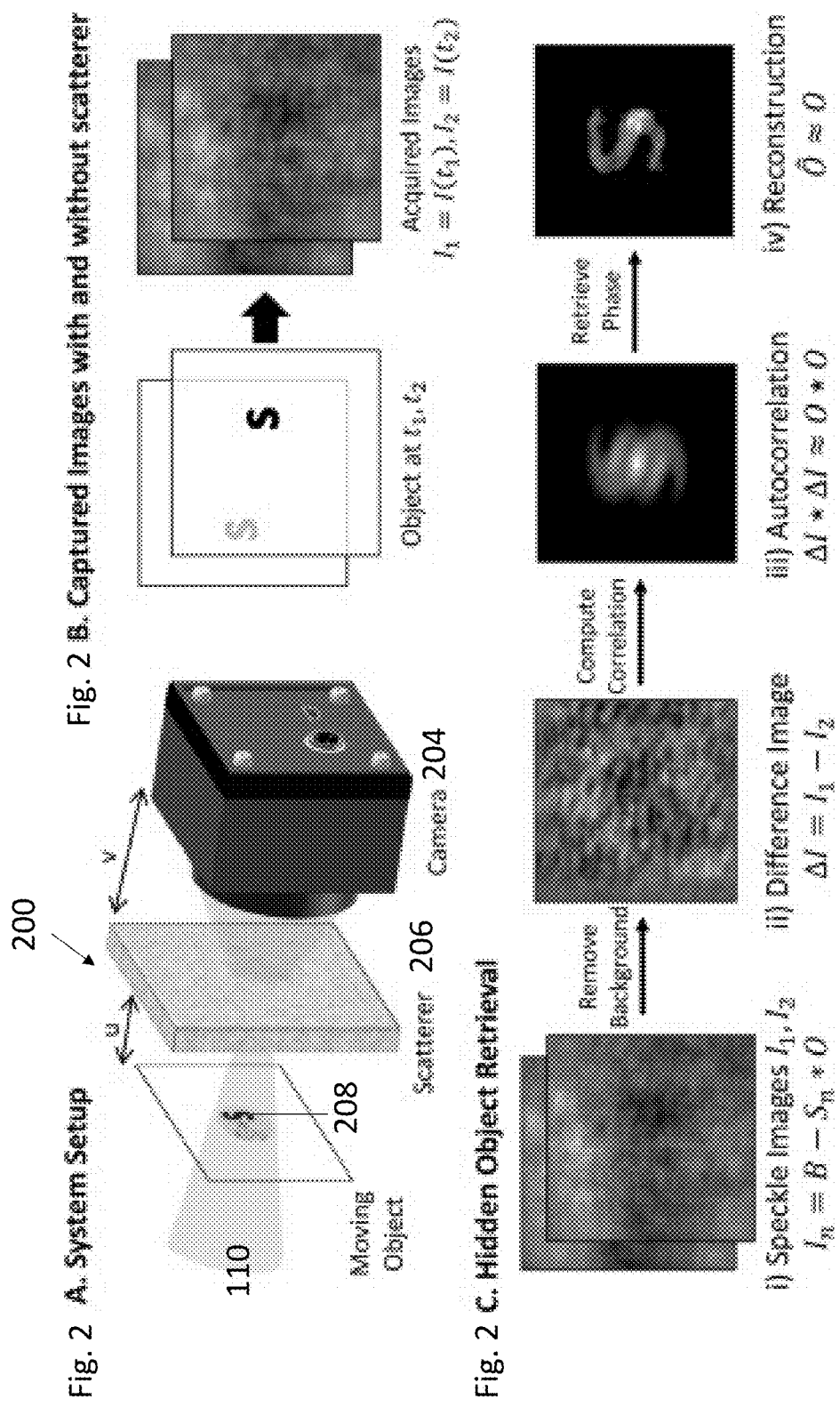

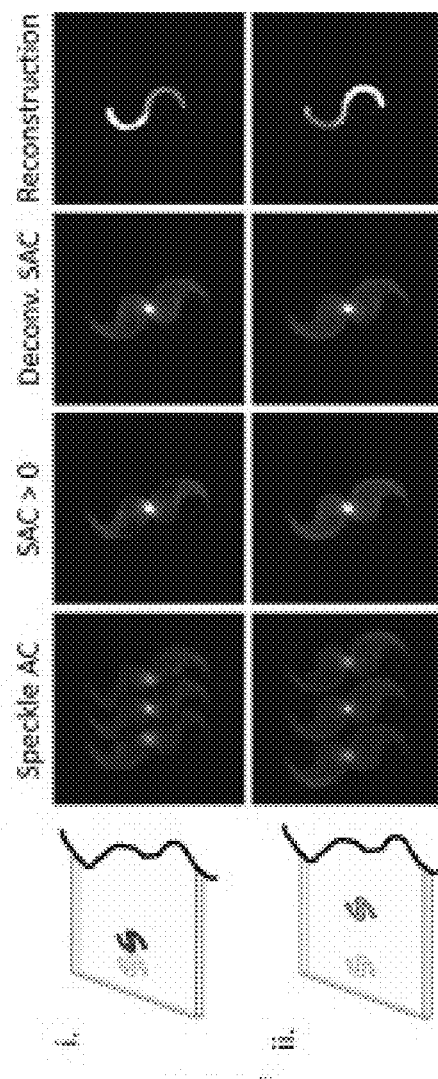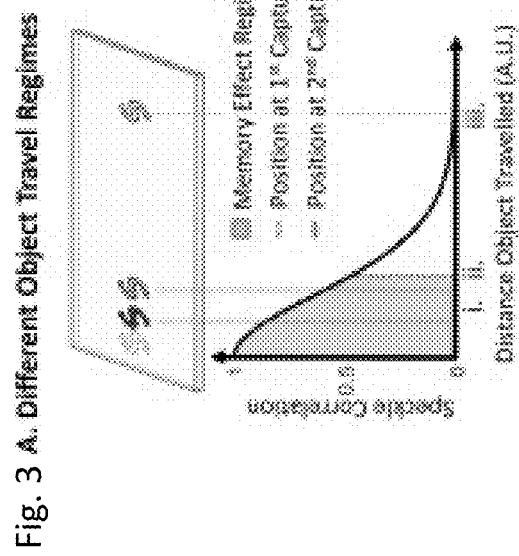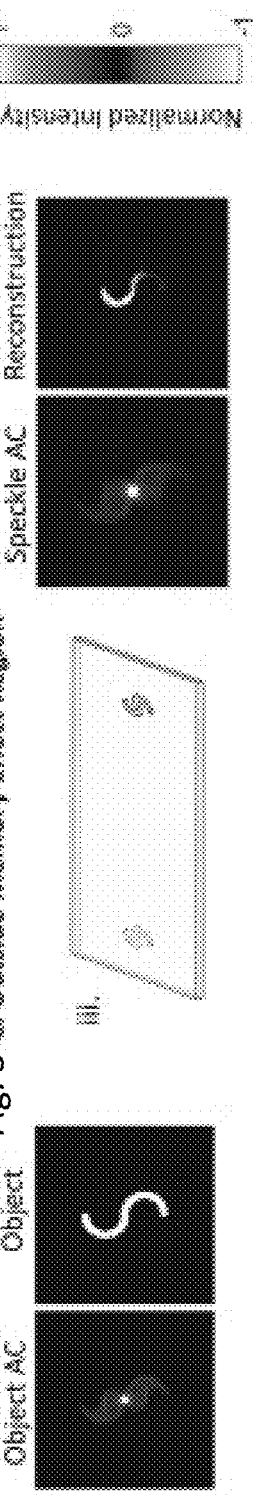
Fig. 3 A. Different Object Travel Regimes
Fig. 3B Inside memory effect region
Fig. 3 C. Outside Memory Effect Region

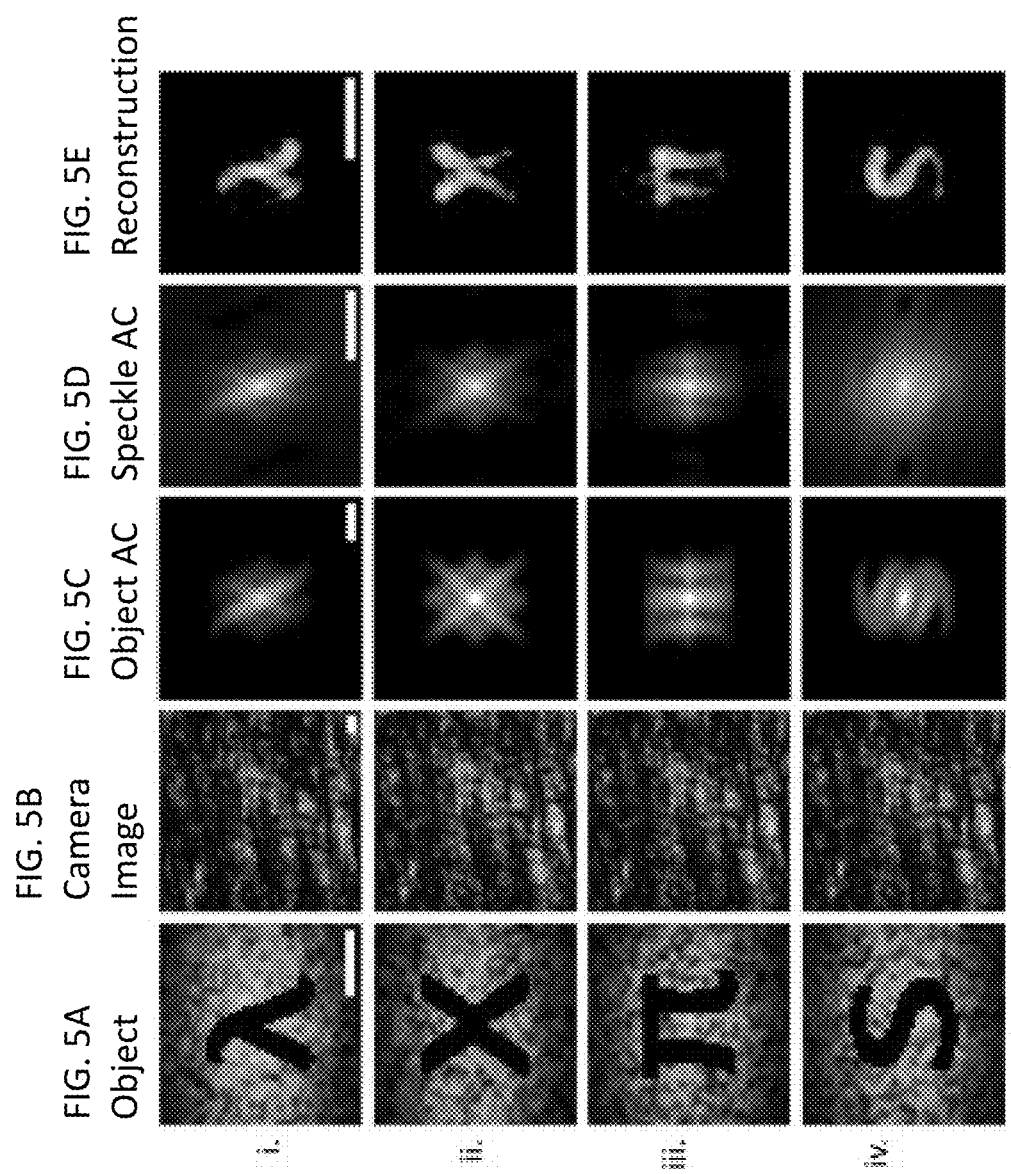

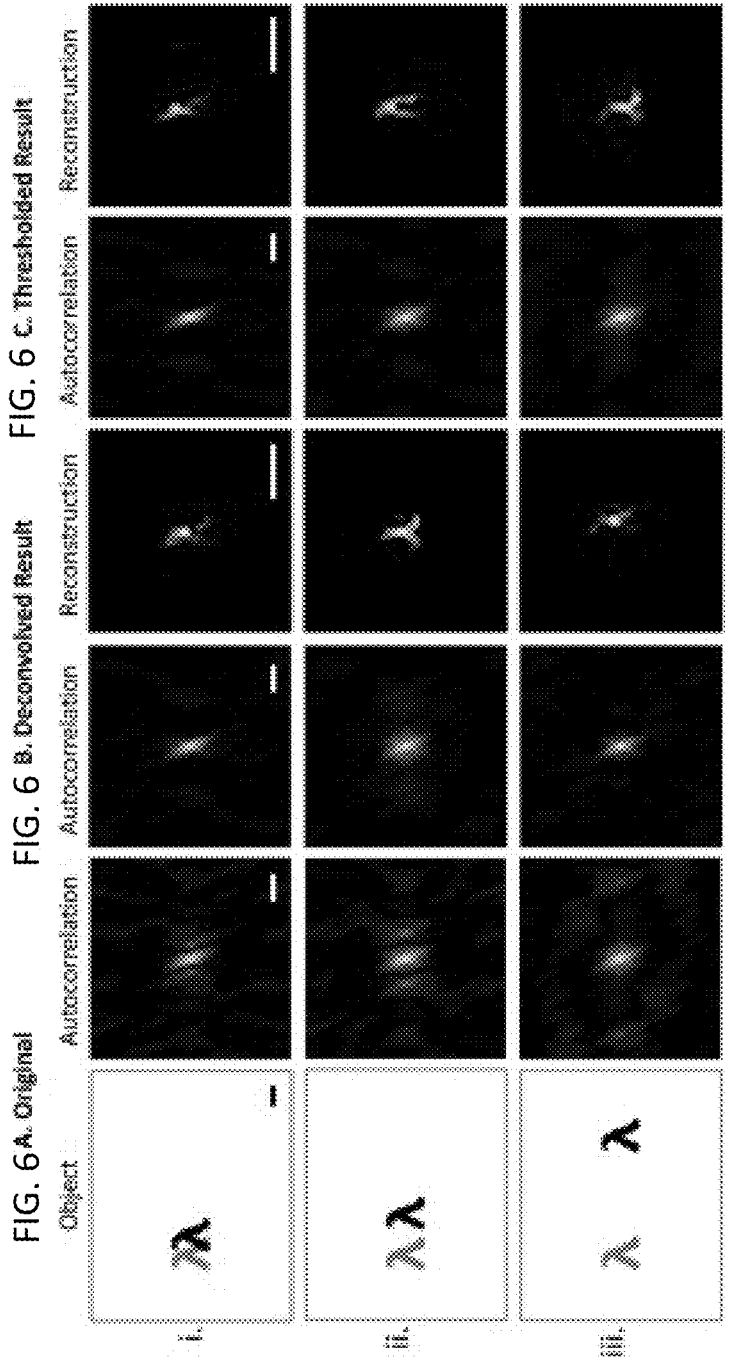

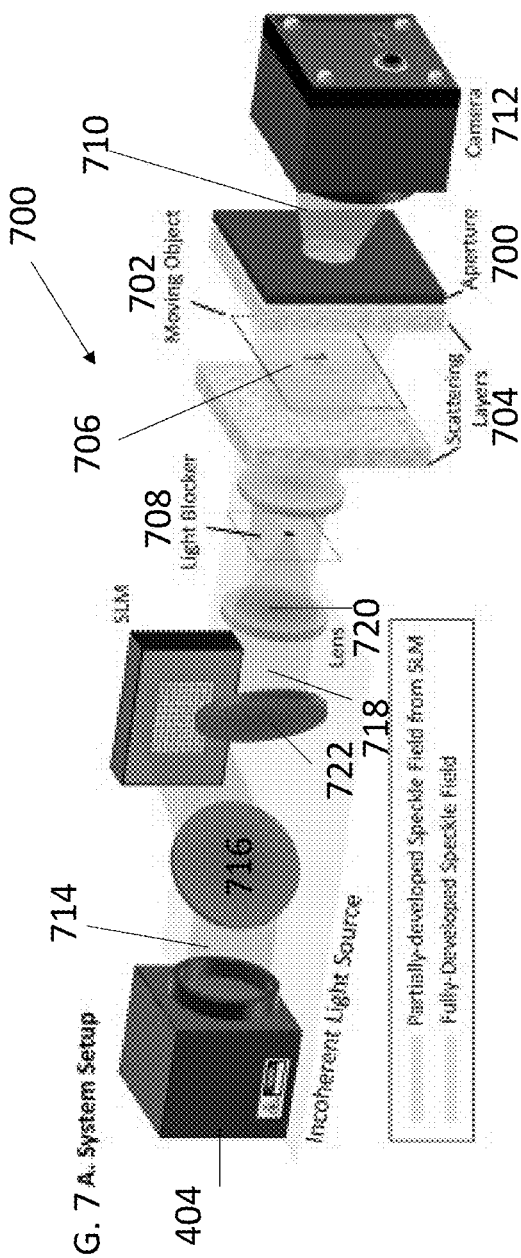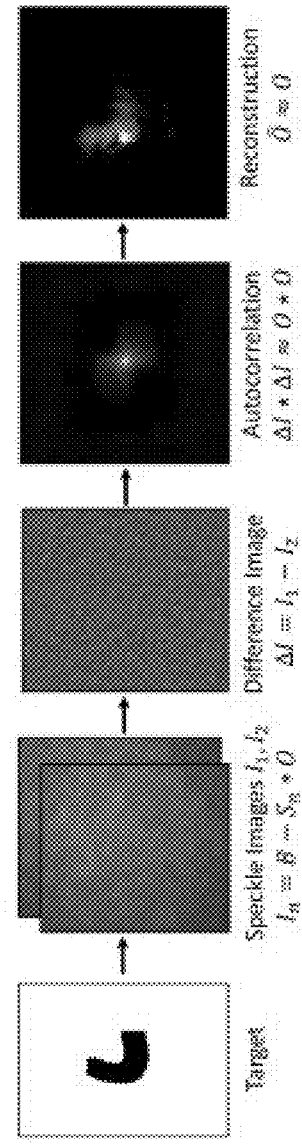
FIG. 7A. System Setup
FIG. 7B. Experimental Result

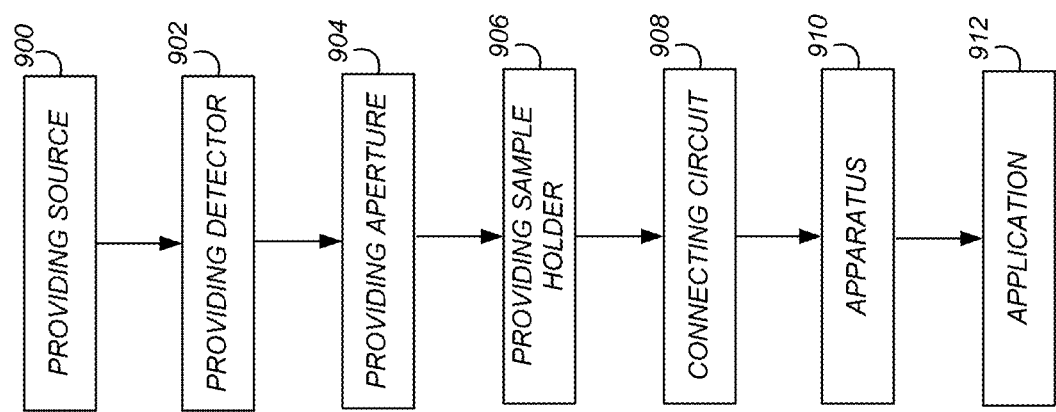

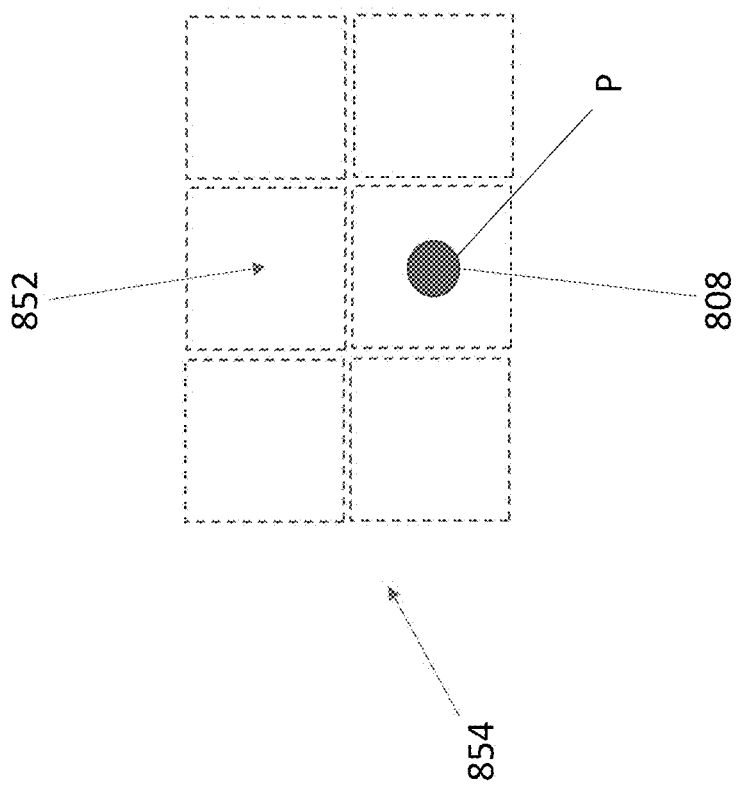

NONINVASIVE, LABEL-FREE, IN VIVO FLOW CYTOMETRY USING SPECKLE CORRELATION TECHNIQUE

CROSS REFERENCE TO RELATED APPLICATIONS

This application claims the benefit under 35 U.S.C. Section 119(e) of commonly-assigned U.S. Provisional Patent Application Ser. No. 62/527,237, filed on Jun. 30, 2017, by Edward H. Zhou and Michelle Cua, entitled "NONINVASIVE, LABEL-FREE, IN VIVO FLOW CYTOMETRY USING SPECKLE CORRELATION TECHNIQUE," CIT-7811), which application is incorporated by reference herein.

STATEMENT REGARDING FEDERALLY SPONSORED RESEARCH AND DEVELOPMENT

This invention was made with government support under Grant No. NS090577 awarded by the National Institutes of Health. The government has certain rights in the invention.

BACKGROUND OF THE INVENTION

1. Field of the Invention

This invention relates to a method and system for imaging and/or performing flow cytometry.

2. Description of the Related Art (Note: This application references a number of different publications as indicated throughout the specification by one or more reference numbers within brackets, e.g., [x]. A list of these different publications ordered according to these reference numbers can be found below in the section entitled "References." Each of these publications is incorporated by reference herein.)

Optical imaging is challenging in turbid media, where multiple scattering of light causes a degradation of resolution and limits the depths at which we can reliably image (<1 mm in biological tissue) without having to resort to destructive optical clearing or sectioning techniques [1]. Many approaches currently exist to filter out the multiply scattered light and detect only the unscattered (ballistic) or minimally scattered photons. These include methods such as time and coherence gating, which separate the ballistic photons from the scattered photons based on their transit time to the detector [2, 3]; methods that rely on preserving the initial angular momentum or polarization modulation [4-7]; and methods that rely on spatial confinement, such as confocal and multi-photon microscopy [1, 8]. An issue with methods that rely on detecting only the minimally scattered photons is the maximum achievable depth of penetration, since the chance of detecting a quasi-ballistic photons decreases exponentially with increasing depth.

Instead of rejecting the scattered photons, other approaches have aimed to take advantage of the information inherent within the detected speckle field that arises from multiply scattered light. Wavefront shaping (WFS) techniques exploit the principles of time-reversal to undo the effect of scattering and enable focusing of light in thick, scattering media [9-12]. However, WFS usually requires long acquisition times to measure the transmission matrix, and/or the presence of a guide star. On the other hand, speckle-correlation-based imaging (SCI) approaches exploit the angular correlations inherent within the scattering process to reconstruct the hidden object and do not need long acquisition times or a guide star [13, 14]. However, SCI methods are limited to working in dark-field scenarios, with sparsely-tagged objects [14], since the detected light must consist solely of light arising from the object.

SUMMARY OF THE INVENTION

To overcome the limitations in the art described above, and to overcome other limitations that will become apparent upon reading and understanding this specification, the present disclosure describes a solution termed speckle correlation flow cytometry (SCFC). By subtracting out the stationary background when shining light through a sample (e.g., a vessel within a biological tissue), light only scattered by the desired targets (e.g., cells) can be captured and different types of targets (e.g., cells) can be distinguished by the autocorrelation of the speckle pattern. In this way, the targets (e.g., cells) can be classified and counted based on the features of their speckle correlations. The technique can be applied not only for noninvasive, label-free, in vivo CTC counting but also for counting other types of blood cells such as white blood cells or red blood cells.

The present disclosure further discloses an apparatus comprising a source of spatially incoherent electromagnetic radiation; a detector positioned to detect (1) a first speckle pattern comprising the spatially incoherent electromagnetic radiation transmitted through a region of a sample including a moving target at a first moment in time; and (2) a second speckle pattern comprising the spatially incoherent electromagnetic radiation transmitted through the region of the sample including the moving target at a second moment in time; and an electronic circuit connected to the detector. The detector outputs a first signal in response to the first speckle pattern and a second signal in response to the second speckle pattern.

The apparatus can be embodied in many ways including, but not limited to, the following embodiments.

1. The circuit determines a difference between the first signal and the second signal used to identify the moving target.
2. The circuit of embodiment 1 autocorrelating the difference to form an autocorrelation, wherein an image/identification of the moving target in the sample is obtained from the autocorrelation using a phase retrieval process
3. The apparatus of one or any combination of embodiments 1-2, wherein the source includes a spatial light modulator.
4. The apparatus of embodiment 3, wherein the spatial light modulator outputs the spatially incoherent electromagnetic radiation comprising a set of spatially uncorrelated phase maps.
5. The apparatus of one or any combination of the embodiments 1-4, wherein the source includes an array of pixels configurable to modulate amplitude and/or phase of electromagnetic radiation reflected from or transmitted through the array, so as to generate the spatially incoherent electromagnetic radiation with a frame rate>1 kHz, each pixel in the array of pixels modulates the incoming electromagnetic radiation 808 to a different phase P so as to generate a random phase map, and a set of the random phase maps was generated, and the map that was displayed on the array of pixels was changed over time in order to decrease the spatial coherence of the electromagnetic radiation, and the detector includes a plurality of pixels disposed in an imaging array so as to capture the first speckle pattern and the second speckle pattern with a detector frame rate>1 kHz.

6. The apparatus of one or any combination of the embodiments 1-5, further comprising a laser for emitting electromagnetic radiation; a collimator coupled to the laser for collimating the electromagnetic radiation so as to form collimated electromagnetic radiation; and a lens or mirror system focusing the spatially incoherent electromagnetic radiation onto the region of the sample, wherein the array of pixels modulates the collimated electromagnetic radiation so as to form the spatially incoherent electromagnetic radiation.

7. The apparatus of one or any combination of the embodiments 1-6, further comprising an aperture between the sample and the detector, the aperture controlling a speckle size of the first speckle pattern and the second speckle pattern on the detector so that a first speckle size of the first speckle pattern and a second speckle size of the second speckle pattern are above a Nyquist sampling limit of the detector.

8. The apparatus of one or any combination of the embodiments 1-7, wherein the detector includes a plurality of pixels disposed in an imaging array, the apparatus further comprising processing logic coupled to the imaging array to initiate capture of the first speckle pattern at the first moment in time T1 and the second speckle pattern at the second moment in time T2, T2-T1 is within a decorrelation time of the sample, and/or within a time for scatterer position shifts within the sample, and/or within 2 seconds.

9. The apparatus of one or any combination of the embodiments 1-8, wherein the detector includes a plurality of pixels disposed in an imaging array, the apparatus further comprising processing logic coupled to the imaging array to initiate capture of the first speckle pattern at the first moment in time T1 and the second speckle pattern at the second moment in time T2, and T2-T1 is such that background speckle intensity components B1, B2 of the first speckle pattern and the second speckle pattern, respectively, formed from a background portion of the spatially incoherent electromagnetic radiation scattered and transmitted through a portion of the sample other than the moving target, are the same to within 1%.

10. The apparatus of one or any combination of the embodiments 1-9, wherein the detector includes a plurality of pixels disposed in an imaging array, the apparatus further comprising processing logic coupled to the imaging array to initiate capture of the first speckle pattern at the first moment in time T1 and the second speckle pattern at the second moment in time T1, the first speckle pattern has an intensity $I_1$ and the second speckle pattern has an intensity $I_2$ $$I_1 = B - O * PSF_1,$$

$$I_2 = B - O * PSF_2,$$

\* denotes convolution,

B is a background speckle intensity image formed from a background portion of the spatially incoherent electromagnetic radiation scattered and transmitted through the sample other than the moving target, $PSF_1$ is a point spread function of a first portion of the spatially incoherent electromagnetic radiation scattered by the moving target at the first moment in time, $PSF_2$ is a point spread function of a second portion of the spatially incoherent electromagnetic radiation scattered by the moving target at the second moment in time, O is a shape of the moving target, the difference is $$\Delta I = I_1 - I_2 = O * (PSF_2 - PSF_1).$$

and the autocorrelation is $$\Delta I * \Delta I = 2(O*O) - (PSF_1 * PSF_2 + PSF_2 * PSF_1) * O = 2(O*O) - \text{noise}.$$

11. A cytometer comprising the apparatus of one or any combination of the embodiments 1-10, further comprising a processor connected to the circuit, wherein the processor identifies the moving target using the difference and counts the moving target.

12. The apparatus of one or any combination of the embodiments 1-11, wherein the moving target is a biological cell and the sample comprises biological tissue.

13. The apparatus of one or any combination of the embodiments 1-12, further comprising a sample holder for holding the sample comprising a blood vessel and wherein the moving target comprises blood cells.

14. The apparatus of one or any combination of the embodiments 1-13, wherein the sample holder includes a clamp clamping the blood vessel so as to control a velocity of blood flow through the blood vessel.

15. The apparatus of one or any combination of the embodiments 1-14, wherein the difference is used to identify the moving target comprising a blood cell or a tumor cell.

BRIEF DESCRIPTION OF THE DRAWINGS

Referring now to the drawings in which like reference numbers represent corresponding parts throughout:

FIG. 2A illustrates a spatially incoherent light source illuminating a moving object hidden behind a visually opaque turbid media. The resultant speckle field is captured by a camera sensor.

FIG. 2B illustrates speckle images are acquired by the camera sensor at different times, with the object moving between the captures. The scattering media prevents resolution of the object using conventional methods.

FIG. 2C illustrates the hidden object can be retrieved from the seemingly random speckle images by taking advantage of inherent angular correlations in the scattering pattern. i) Each captured image $I_n$ consists of a background, B, subtracted by the imaged object, where the imaged object is the convolution of the PSF of the scattering media, S, and the object pattern, O. ii) Although the background signal dominates over the object, it can be subtracted out by taking the difference between the two captured images ΔI. iii) The object autocorrelation O★O is approximated by autocorrelating the difference image ΔI. iv) The hidden object can be reconstructed from the object autocorrelation by using phase retrieval techniques.

FIGS. 3A-3C. Impact of object travel distance on the computed speckle autocorrelation (SAC). FIG. 3A: The scattering PSFs experienced by an object have a degree of correlation $C(\Delta x)$ that depends on the distance the object traveled. When $C(\Delta x) \geq 0.5$ (shown in red), the object is considered to have traveled within the memory effect (ME) region. For comparison, the object and its autocorrelation (AC) are displayed. FIG. 3B: When the object travels inside the ME region, the SAC contains three copies of the object autocorrelation (OAC): a centered, positive copy and two negative copies shifted by an amount proportional to the object travel distance. The OAC can be determined by either deconvolving the SAC or by thresholding out the negative portions (negative with reference to the mean, background level). The object can be reconstructed from the estimated OAC using phase retrieval techniques. FIG. 3C: When the object travels a distance where $C(\Delta x) \approx 0$, only a single copy of the OAC is seen, with additional noise from the cross-correlation between uncorrelated PSFs. The normalized colormap used to display the AC and reconstructed object, with 0 corresponding to the mean background level.

FIGS. 5A-5C: Experimental imaging of moving targets hidden behind a diffuser. FIG. 5A shows the "object" is hidden behind a scattering medium and attenuates light transmission (the object was moved 1.5 mm between acquisitions. FIG. 5B: Due to the presence of the scattering medium, the object is obscured, and the camera image $I_1$ is dominated by the scattered light from the background. FIG. 5C: The ideal object autocorrelation (AC). FIG. 5D: The speckle autocorrelation $\Delta I \star \Delta I = O \star O$. E) By applying phase retrieval on the speckle autocorrelation, the hidden object was reconstructed with high fidelity. Scale bar=500 µm.

FIGS. 6A-6C: Experimental results showing the effect of object motion distance on the speckle autocorrelation (SAC) and object reconstruction. FIG. 6A: A diagram showing the position and shape of the object at both time captures, and the SAC, showing three shifted copies of the object autocorrelation (OAC). The effect of applying (FIG. 6B) deconvolution and (FIG. 6C) thresholding to retain the positive portion (with respect to the mean level) for estimating the OAC from the SAC was compared in three cases (i-iii). The hidden object was reconstructed by applying Fienup phase retrieval on the estimated OAC. Colormap: green is positive, blue is negative (with respect to the mean value, in black). Scale bar: 500 µm.

FIGS. 7A-7B: Experimental retrieval of moving targets hidden within a scattering object. FIG. 7A: Schematic of the experimental setup. A spatially incoherent light source is generated by reflecting an expanded laser beam off a spatial light modulator (SLM) that applied a temporally variant random phase pattern. The partially developed speckle field component is blocked, and only the fully-developed speckle field transmits through the moving object and two scattering layers. The emitted scattered light is collected by a camera. An aperture controls the resolution and the speckle size at the camera. FIG. 7B: Experimental result of a moving target. Two speckle intensity images, $I_1$, $I_2$, were captured, with the target present for the first capture, and absent for the second.

The background halo from $I_1$ and $I_2$ were removed prior to computing the difference $\Delta I = I_2 - I_1 \approx S_1 * O$. The speckle autocorrelation yielded an estimate of the object autocorrelation, from which the target was retrieved by applying Fienup phase retrieval. Lens focal length=400 mm.

Figure 8:
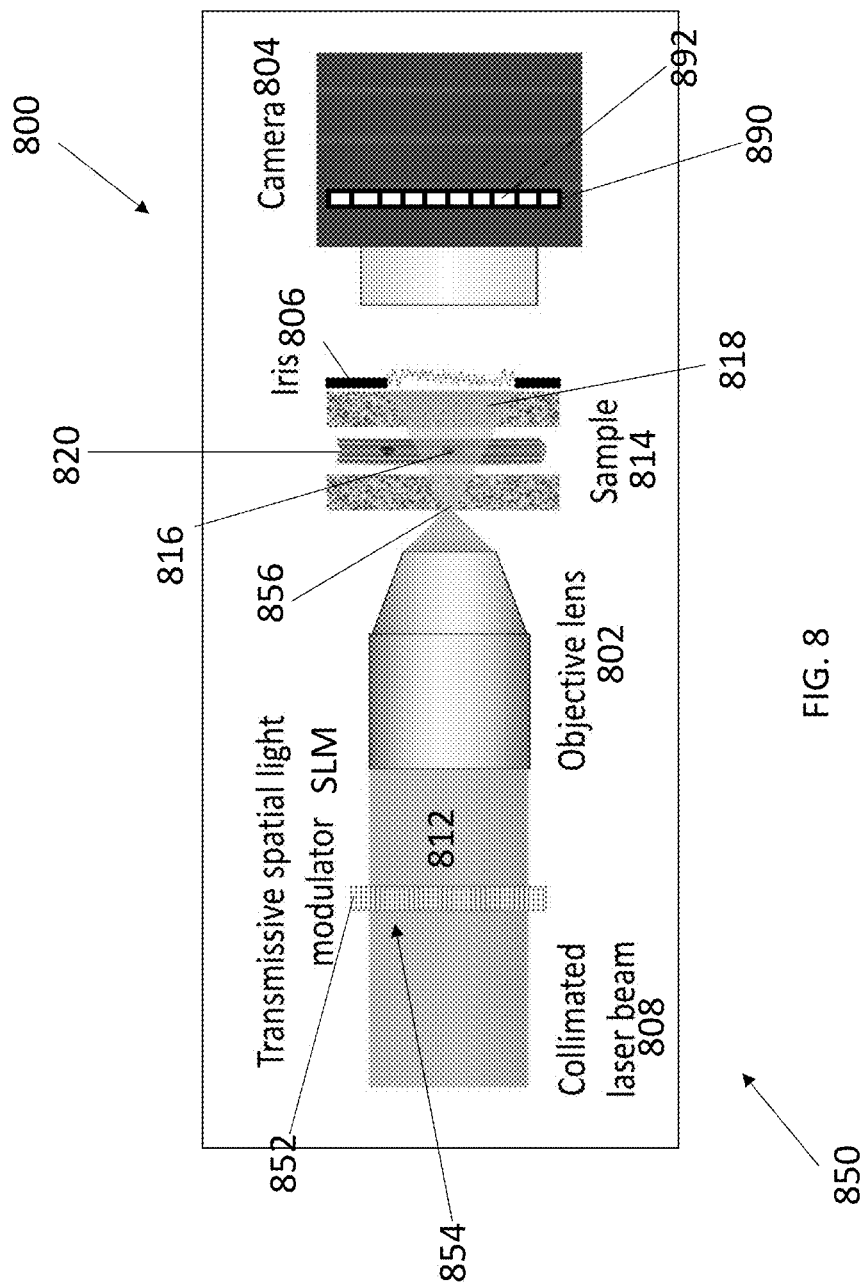

FIG. 8. Apparatus for performing SCFC according to one or more embodiments.

FIG. 9A is a flowchart illustrating a method of fabricating an apparatus according to one or more embodiments of the present invention.

FIG. 9B is a schematic illustrating formation of the spatially incoherent electromagnetic radiation.

Figure 10:
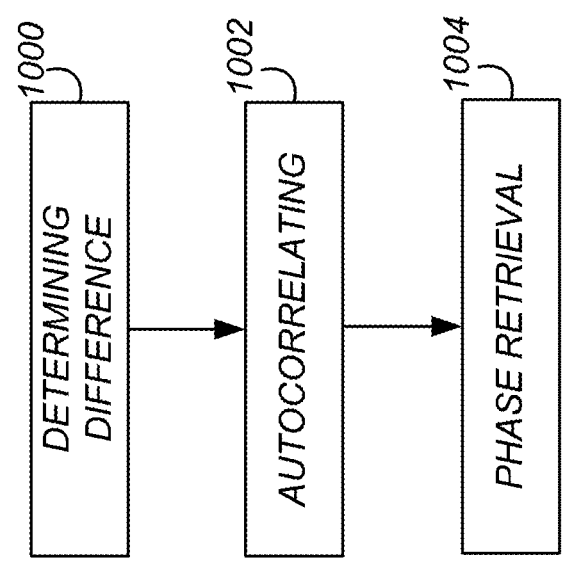

FIG. 10 illustrates a method of identifying a moving target in a sample.

Figure 11:
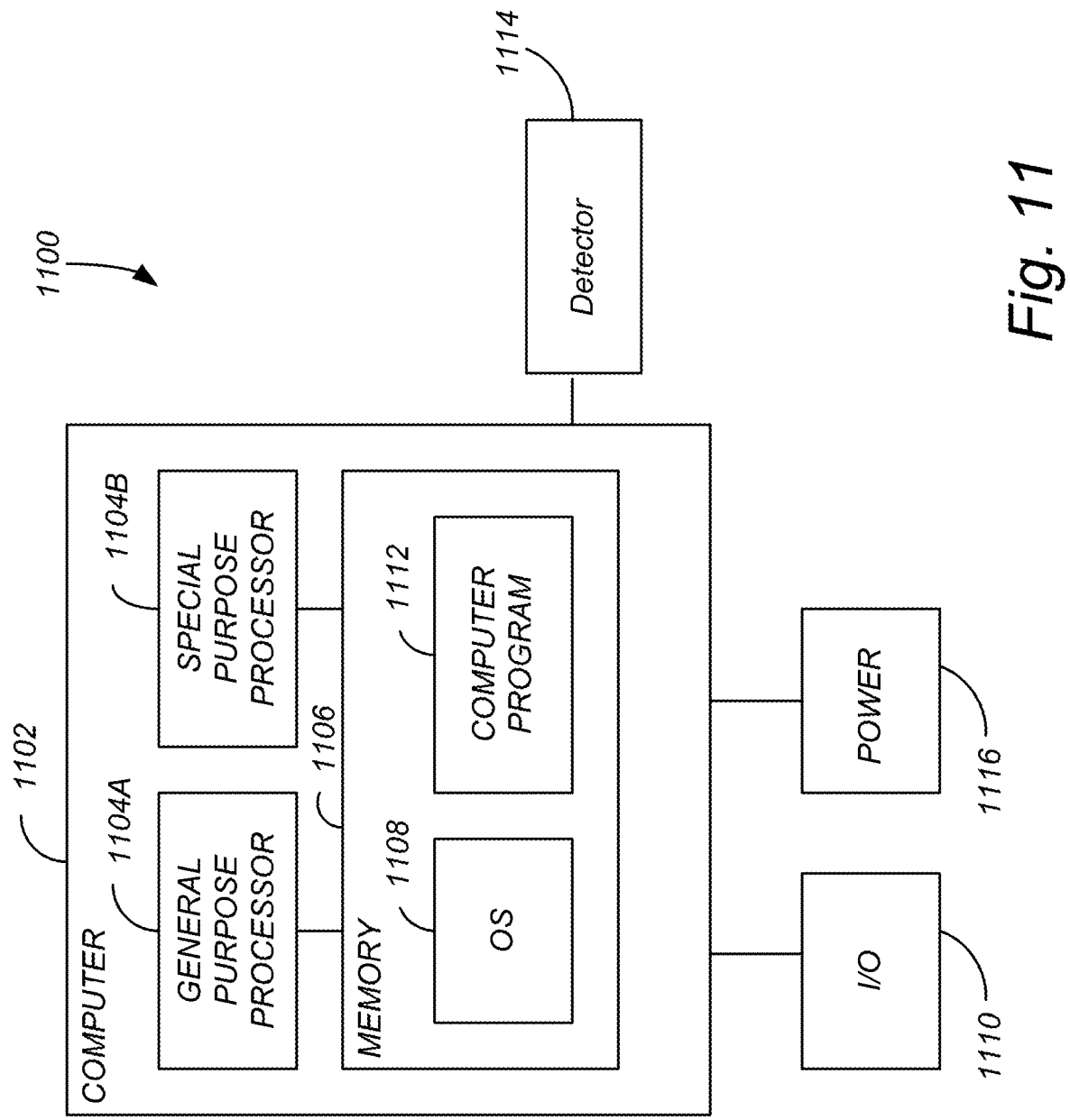

FIG. 11 illustrates a hardware environment for implementing the processing functions described herein.

DETAILED DESCRIPTION OF THE INVENTION

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Technical Description

Figure 1:
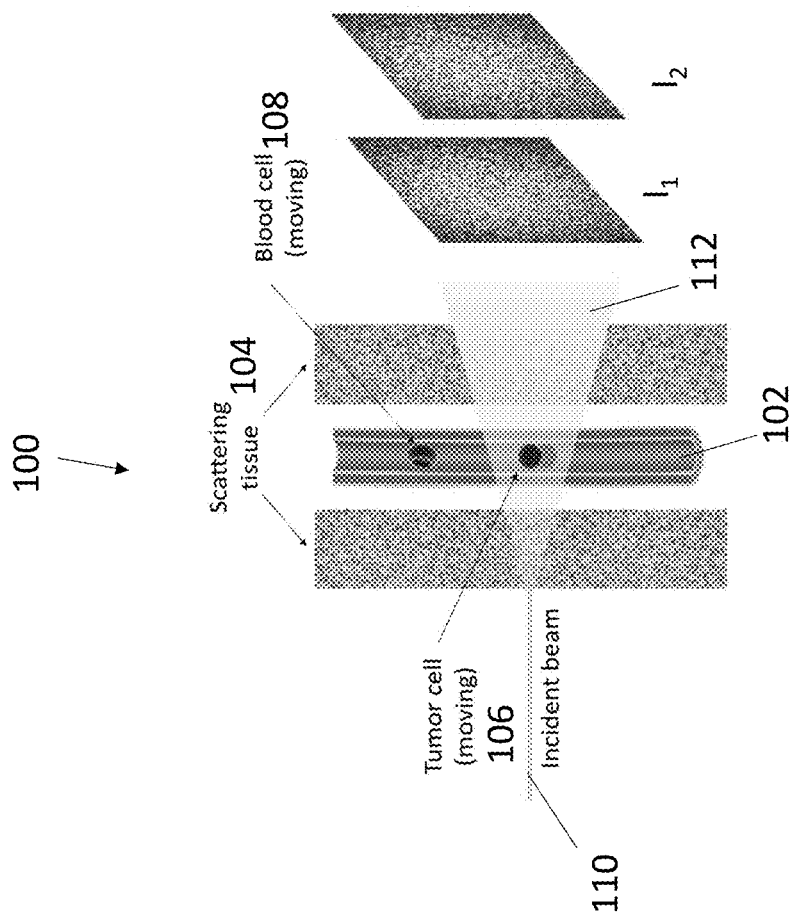
FIG. 1 illustrates a scenario of in vivo speckle correlation flow cytometry.

The basic principle of the SCFC technique is rooted in the speckle correlation imaging technique [14]. The in vivo flow cytometry scenario 100 shown in FIG. 1 can be used to explain the principle. FIG. 1 illustrates a thin blood vessel 102 within a scattering biological tissue 104, wherein the vessel 102 is thin enough to allow cells (tumor cell 106 and blood cells 108) to flow or move through the vessel 102 sparsely one after another. Due to the scattering of the tissue 104, it is difficult to realize diffraction limited imaging of the cells by conventional methods. Moreover, due to the restriction of labeling, light passing through different types of cells cannot be distinguished by fluorescent spectroscopy. In SCFC, a spatially incoherent single wavelength beam 110 is incident on the sample. Due to the scattering of the tissue, the incident beam will form a scattered beam 112 measured at an output as a speckle pattern $I_1$. Within the tissue, the incident beam will form a speckle field on the plane of the blood vessel. If the size of the cell is smaller than the memory effect range [37-40] of the scattering sample, the output speckle patterns ($I_1$ and $I_2$) captured at two different moments when there is a cell moving in the speckle field can be expressed as $$I_1 = B - O * \text{PSF}_1,$$

$$I_2 = B - O * \text{PSF}_2,$$

where * denotes convolution, B is the speckle intensity image arising from the scattered light transmitted through the tissue, $I_1$ is the speckle pattern measured at a first moment in time, $I_2$ is the speckle pattern measured at a first moment in time, $\text{PSF}_1$ is the point spread function of the light scattered by the cell 106, 108 (or equivalently the speckle intensity distribution a single point source in the memory effect region) the first moment in time, $\text{PSF}_2$ is the point spread function of the light scattered by the cell 106, 108 at the second moment in time, and O is the shape of the cell. As long as the rest of the sample is static, the speckle field arising from the background will remain unchanged and can be subtracted out by taking the difference between captures. That is, $$\Delta I = I_1 - I_2 = O*(PSF_2 - PSF_1).$$

Since the scattering PSF is a delta correlated process PSF*PSF=δ, taking the autocorrelation (denoted as *) of ΔI yields the object autocorrelation, plus additional noise terms. That is, $$\Delta I * \Delta I = 2(O*O) - (PSF_1 * PSF_2 + PSF_2 * PSF_1) * O = 2(O*O) - \text{noise}.$$

The object can be recovered from the speckle autocorrelation by using phase retrieval techniques, such as the Fienup iterative phase retrieval methods [41].

First Example

FIG. 2A illustrates an example apparatus 200 for performing SCFC, illustrating the scattered light 202 is detected by a high-resolution camera 204 that is placed at a distance v from the scattering media 206 and wherein the moving object 208 is at a distance u from the scatterer. The resultant object will have an image size dictated by the magnification of the system, M=−v/u.

FIG. 2B illustrates captured images with and without the scatterer.

FIG. 2C illustrates the hidden object can be retrieved from the seemingly random speckle images by taking advantage of inherent angular correlations in the scattering pattern. FIG. 2C(i) shows each captured image $I_n$ consists of a background, B, subtracted by the imaged object, where the imaged object is the convolution of the PSF of the scattering media, S, and the object pattern, O. FIG. 2C(ii) shows that, although the background signal dominates over the object, it can be subtracted out by taking the difference between the two captured images ΔI. FIG. 2C(iii) shows the object autocorrelation O★O is approximated by autocorrelating the difference image ΔI. Since the scattering PSF is a delta-correlated process $(S_n(x) \star S_n(x) \approx \delta(x))$, taking the autocorrelation (AC) of the image ΔI yields the object autocorrelation (OAC), plus additional noise terms. FIG. 2C(iv) shows the hidden object can be reconstructed from the object autocorrelation by using phase retrieval techniques (such as the Fienup iterative phase retrieval methods) that recover the Fourier phase [17].

Second Example: Effect of Travel Distance

Depending on the distance traveled by the object, the PSFs $S_n$, n=1, 2, . . . may or may not be correlated. FIGS. 3A-3C illustrate the effect of travel distance, relative to the ME range, on the SAC. The speckle intensity images $I_1$, $I_2$ were determined using simulation. For comparison, the autocorrelation of the object/target, A=O★O has also been provided [FIG. 3A, "Object AC"]. For simplicity, only the case of two image captures (n=1, 2) has been considered.

For a moving object, the associated PSFs $S_1$, $S_2$ will have a degree of correlation C(Δx) based on the object travel distance Δx. For scattering media with thicknesses L greater than the mean free path, the degree of correlation can be approximated using the angular correlation function $$C(\Delta x) = \left[\frac{k\Theta L}{\sinh(k\Theta L)}\right]^2 \quad (6)$$

where k=2π/λ, L is the thickness of the scattering medium, and Θ≈Δx/u [18-20]. When C(Δx)>0.5, the object is considered to have traveled within the ME field of view. The following sections describe three possible cases in more detail: C(Δx)≈1, C(Δx)>0.5, and C(Δx)→0.

Case 1: Object Travels Distance Where C(Δx)Δ1

In the case where the object travels a small distance (such that C(Δx)≈1), we have $$S_2(x_i) \approx S_1(x_i + \Delta x_i) \quad (7)$$

where x=(x, y), $x_i=(x_i, y_i)$ are coordinates in the object plane and image plane respectively, Δx is the distance the object traveled in the object plane, and $\Delta x_i = M\Delta x$. We can equivalently consider the PSF to be the same in both captures and have the object travel between captures. That is, $$O_2 = O(x_i + \Delta x_i), \quad (8)$$

$$\Delta I = S * [O(x_i) - O(x_i + \Delta x_i)], \quad (9)$$

and $$\Delta I * \Delta I = 2A(x_i) - A(x_i + \Delta x_i) - A(x_i - \Delta x_i). \quad (10)$$

where A=O★O is the object, autocorrelation (OAC). The SAC contains three copies of the OAC: a positive copy centered at x=(0, 0), and two negative copies shifted by an amount commensurate with the object travel distance [FIG. 5B, "Speckle AC")].

Since C(Δx)≈1 when Δx≈0, the object may travel a distance shorter than the extent of its autocorrelation. In this case, the SAC will yield positive and negative copies of the OAC that overlap [FIG. 3Bi]. The OAC can be recovered using deconvolution [FIG. 3Bi, "Deconv. SAC."]. Using thresholding to remove the negative portions will adversely impact the positive copy and result in an incomplete estimation of the OAC [FIG. 3Bi, "SAC>0"]. For the results presented in FIG. 23, the objects were reconstructed by applying an iterative phase retrieval algorithm on the deconvolved SAC ([13, 14, 17]).

Case 2: Object Travels Distance Where C(Δx)>0.5

In the regime where the object travels within the angular ME range (C(Δx)>0.5), $S_1$ and $S_2$ are correlated. To highlight the impact of the degree of correlation C(Δx) on the SAC, we can mathematically represent $S_2$ as:

$$S_2 = C(\Delta x) S_1(x_i + \Delta x_i) + \sqrt{1 - [C(\Delta x)]^2} S, \quad (11)$$

where S is a speckle intensity pattern that is uncorrelated with $S_1$. The scatter PSFs in the equation above are mean-subtracted speckle intensities. Representing $S_2$ in the form above allows us to preserve speckle intensity statistics (that is, the speckle intensity variance and mean satisfy $\mathbb{V}[S_1]=\mathbb{V}[S_2]$ and $\mathbb{E}[S_1]=\mathbb{E}[S_2]$ respectively.)

Using Eq. (11), Eqs. (4) and (5) become $$\Delta I = (S_1 - C(\Delta x) S_1(x_1 + \Delta x_i) - \sqrt{1-[C(\Delta x)]^2} S) * O \quad (12)$$

and $$\Delta I \star \Delta I \approx 2A(x_i) - C(\Delta x) A(x_i \pm \Delta x_i) + \sqrt{1-[C(\Delta x)]^2} \times \text{noise}, \quad (13)$$

where the last equation follows from noting that the speckle fields are a delta-correlated process and that the cross-correlation of two uncorrelated speckle intensities yields noise.

The SAC still contains three copies of the OAC. However, the ratio of the intensity of the positive and negative OAC copies is determined by the ME correlation function $C(\Delta x)$. Moreover, since $S_2 \neq S_1$, there is an additional noise term that increases with decreasing $C(\Delta x)$. Since there is no overlap between the positive and negative OAC copies, the OAC can be retrieved by either thresholding out the portions of the SAC that are smaller than the background value [FIG. 3Bii, "SAC>0")], or by deconvolving the image [FIG. 3Bii, "Deconv. SAC.")]. The sixth example provides more details on the deconvolution algorithm.

Case 3: Object Travels Distance Where $C(\Delta x) \approx 0$

In the case where the object travels outside the memory effect region between captures, $S_1$ and $S_2$ are uncorrelated, and Eq. (13) can be simplified as Eq. (5). Comparing the SAC in FIG. 3Ciii with those in FIG. 3Bi-ii, we see that the SAC in the case where the object travels farther than the ME region exhibits more noise. This is expected due to the additional noise term caused by $S_1 \star S_2$ that is not present in Case 1.

From above, in all cases (for $C(\Delta x) \in [0, 1)$), we can successfully retrieve the object autocorrelation from the acquired speckle images, $S_1$, $S_2$. From the estimated OAC, phase retrieval techniques can then be applied to reconstruct the object at diffraction-limited resolution.

Third Example

Figure 4:
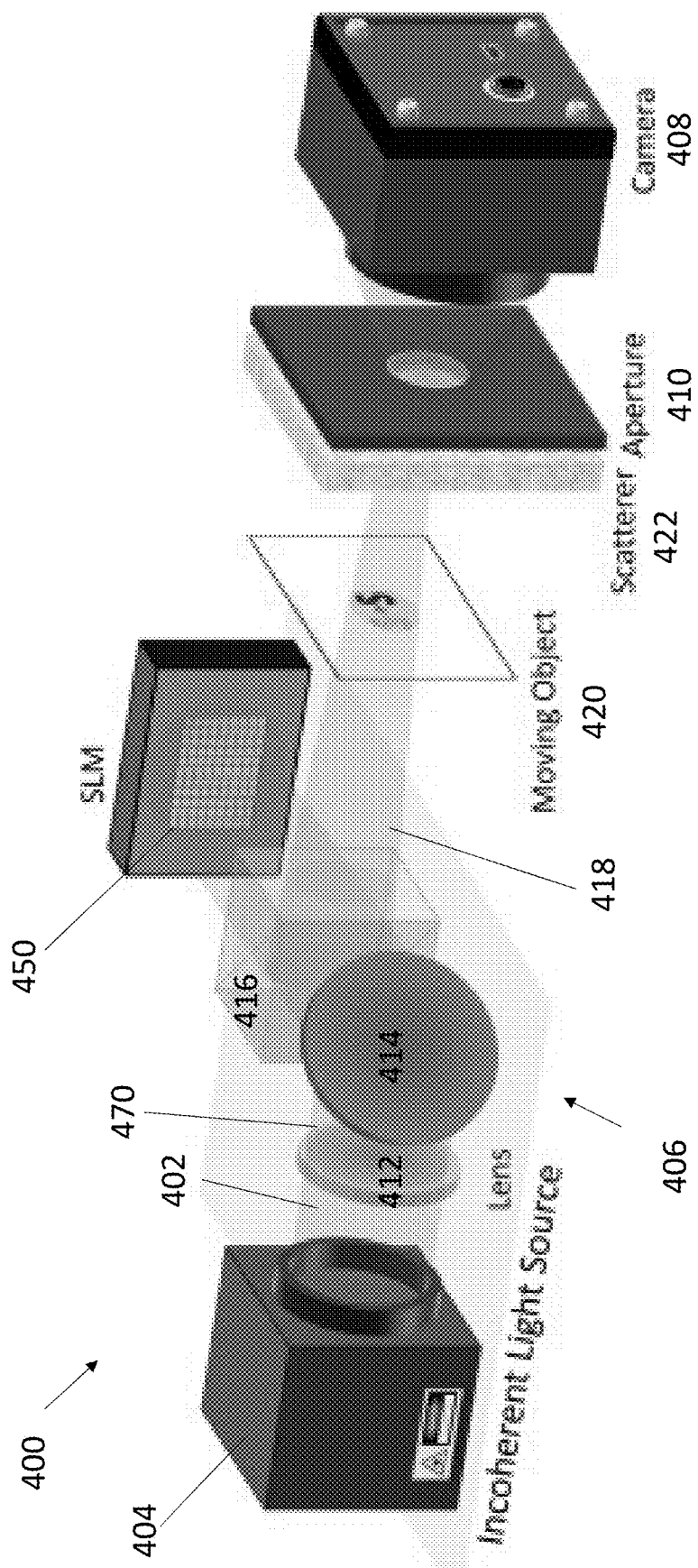
FIG. 4 Experimental setup for imaging hidden moving objects. A spatially incoherent source is generated by reflecting an expanded laser beam ($\lambda$=532 nm; 1/e² diameter of 20 cm) off a spatial light modulator (SLM), which applies a temporally varying set of random phase patterns. The light source is transmitted through the moving object and scattered by the turbid media. The emitted scattered light is collected by a camera. An aperture controls the final object resolution and the speckle size at the camera. Lens focal length=400 mm.

FIG. 4 illustrates an apparatus 400 for performing SCFC according to one example. In this demonstrative example, a laser light beam 402 emitted from a laser 404 (CrystaLaser CS532-150-S; $\lambda$532 nm) was expanded (1/$e^2$ diameter of 20 cm) and reflected off a phase-only spatial light modulator (SLM; Holoeye PLUTO-VIS) to generate a spatially incoherent light source 406 as illustrated in FIG. 4. The apparatus 400 further includes a camera 408 and an aperture 410, a lens 412, a mirror 414 (for directing beam 402 towards SLM), and a beamsplitter 416 for directing the beam 402 onto the SLM and directing the spatially incoherent light 418 reflected from the SLM towards the moving object 420 and the scatterer 422.

The SLM was used in place of a rotating diffuser in order to generate a deterministic, temporally variant set of 50 to 100 random phase patterns. This set of patterns was used for all the acquisitions to ensure that the background light captured remained constant. FIG. 4 further illustrates the moving object 420 and camera 408 (pco.edge 5.5, PCO-Tech, USA) were placed at a distance u=20–30 cm and v=10–15 cm from the scattering media (DG10-120 diffuser; Thorlabs, USA) respectively (FIG. 4).

To ensure that only the object 420 moved between successive image captures, a transmissive SLM (tSLM; Holoeye LC2002 with polarizer) coupled with a polarizer (Thorlabs, LPVISE200-A) was used for amplitude modulation, and served as the object (FIG. 5). For each object, a set of n=4 images, $I_1, \ldots I_4$ were acquired, with the object moving 1.5 mm between each acquisition. The raw camera images [FIG. 5B] display a seemingly random light pattern that is similar for different objects. This is due to the dominant contribution of the background.

From each successive pair of acquired images, the OAC [FIG. 5D] was estimated by deconvolving the SAC. The deconvolved SAC images were then averaged to reduce noise and yield a better estimate of the OAC. Fienup-type iterative phase retrieval method was applied to reconstruct the hidden object with high fidelity [FIG. 5E] [13, 14, 17]. One modification that was made to the algorithm was to add an object support to the object constraints; this object support was determined from the OAC support [21, 22]. In all cases, the obscured object was successfully reconstructed [FIG. 5E].

To experimentally demonstrate the effect of object travel distance, we moved an object a distance of 0.5, 1, and 3 mm between image acquisitions, and looked at the corresponding SAC and reconstructed object (FIG. 6A-6C). As expected, the SAC contained three copies of the OAC. We also compared the effect of processing the SAC using deconvolution [FIG. 6B] vs. thresholding [FIG. 6C].

For Case i, the object traveled a distance $\Delta x < \delta x$, and both the object and SAC overlapped in space between successive acquisitions. In the case of object overlap, only the non-overlapping portion of the object can be retrieved [FIGS. 6A-Ci]. Comparing the result of deconvolution vs thresholding, the reconstructed image from the deconvolved SAC more closely resembles the original object [FIG. 6Bi]. However, in both cases, what we are left with is an incomplete OAC and reconstructed object.

For Case ii, the object traveled a distance $\delta x < \Delta x \leq 2\delta x$. Since the OAC support is approximately twice the object support, the positive and negative copies of the OAC overlapped [FIG. 6ii)] [21]. Due to the overlap, thresholding resulted in an imperfect object reconstruction [FIG. 6Cii]. In contrast, by deconvolving, the signal from the negative copies can be used to gain a better estimate of the OAC, from which the object can be reconstructed [FIG. 6Bii].

For Case iii, the object traveled a distance $\Delta x \gg 2\delta x$, and there was no overlap in the SAC. Due to the large $\Delta x$, $C(\Delta x)$ decreased, and correspondingly, the noise increased. Since the signal-to-noise ratio (SNR) of the negative copies decreased, the entire OAC cannot be seen in the negative copies [FIG. 6Aiii]; thus, performing a deconvolution results in a noisy, imperfect OAC [FIG. 6Biii], and it is more advisable to use thresholding to retain only the positive portion of the SAC [FIG. 6Ciii]. If we compare the reconstructed objects in both cases, we see that the object from the thresholded result more closely resembles the original object.

Fourth Example

FIG. 7 illustrates a further apparatus 700 for demonstration of the imaging technique, wherein a moving object 702 is placed between two diffusers (Newport 10° Light Shaping Diffuser, Thorlabs DG10-220-MD) [FIG. 7A] acting as scattering layers 704. The moving object 702 (a bent black wire) was flipped in and out of the light path 706 between image captures, such that $I_2 = B$. We blocked the partially-developed speckle field (from the propagation of the SLM phase pattern) using a light blocker 708 and used only the fully-developed speckle pattern [23]. This fully-developed speckled pattern was transmitted through both scattering media 704 and the moving object 702. The emitted scattered light 710 was detected by a camera 712. The apparatus 700 further includes a laser 404 emitting light 714, an SLM, a mirror 716 directing the light 714 onto the SLM, wherein the SLM reflects and modulates the light 714 to form a reflection including spatially incoherent light 718, mirror 722 directing spatially incoherent light 718 towards the moving target 702, and lens 720 focusing the light 718 onto the moving object 702.

The background halo from each detected speckle intensity image was estimated and removed by performing Gaussian filtering (500×500 kernel, σ=100), and then dividing each image by the background halo [14]. The SAC was then computed to estimate the OAC, from which phase retrieval was applied to reconstruct the hidden object. Although the object is fully obscured from both sides by scattering media and cannot be resolved from the camera image alone, using our technique, we were able to successfully reconstruct the hidden object with high fidelity [FIG. 7B].

Fifth Example

FIG. 8 illustrates another effective approach for SCFC, utilizing an apparatus 800 comprising a transmissive spatial light modulator (SLM), an objective lens 802 electromagnetically coupled to the SLM, a camera 804, an iris 806 electromagnetically coupled to the camera 804. A collimated laser beam 808 passes through the transmissive SLM in such a way that a spatially incoherent single wavelength light source 810 is constructed as needed. The collimated laser beam 808 transmitted through SLM is modulated by the SLM to form a spatially incoherent light 812. The objective lens 802 is used to confine the incident light 812 to a small area on the sample 814, so that only one cell 816 in the sample 814 is illuminated by spatially incoherent light 812 travelling through the sample 814. The light 818 focused on the sample 814 propagates through the sample 814 diffusively and presents as a speckle pattern on the other side of the sample 814. The speckle pattern is captured by the camera 804.

The iris 806 is placed on the sample 814 to control the speckle size on the camera's 804 sensor chip, so that the speckle size is above the Nyquist sampling limit of the camera.

During every exposure of the camera 804, the SLM displays a series of pre-set spatially uncorrelated phase maps to guarantee the backgrounds O are the same in each frame. When there is a cell 816 flowing through the vessel within the sample, ΔI can be acquired by subtracting two adjacent captured frames as aforementioned. Then, ΔI*ΔI is calculated computationally and the target cell 816 is classified based on the features of ΔI*ΔI as shown in FIG. 5A-5E. By repeating the process on a group of cells, a cytometry result can be acquired.

In operation, to guarantee the motion of the cells 816 is slow enough to be captured by the camera, the target blood vessel can be pinched to control the velocity of blood flow. In one or more examples, for the cells to flow through one after another, a thin blood capillary can be chosen as a target vessel 820. To prevent light beam 818 transmitting through the sample 814 from diffusing too much to cover several cells, a thin pinch of skin or the earlobe will be a suitable sample area.

During capturing the speckle pattern, a stable background is required for subtraction. As living tissues are decorrelating all the time [42], a camera exposure time much shorter than the decorrelation time of the sample is required to overcome the decorrelation. Moreover, since the throughput of the cytometry system depends on the frame rate of the camera, a high frame rate camera with fast shutter is required for the system. PCO.dimax S1 [43] can be an option, from which a throughput of 2200 cells per second is expected.

FIG. 5A-5E shows a group of objects that can be retrieved through the technique described in this fifth example. From column C and column E, we can tell the speckle autocorrelation is identical to the speckle correlation as predicted. A disadvantage of the speckle correlation imaging technique it that phase retrieval is computation intensive and time consuming. For example, in the experiment, to retrieve a single object takes ~10 mins. Speckle correlation imaging technique is difficult to cope with a large population of cells required for metastasis prognostic. However, for flow cytometry, instead of imaging, we only need to distinguish the objects from each other. Different objects can be classified by comparing their respective speckle correlation, which will largely save the computation time. Therefore, SCFC can be a solution to noninvasive, label-free, in vivo flow cytometry.

Sixth Example: Deconvolving the Speckle Autocorrelation

To deconvolve the speckle autocorrelation (SAC), ΔI★ΔI, Weiner deconvolution was applied to reduce the deconvolution noise. We briefly describe the process here. We can rewrite Eq. (13) as $$g = \Delta I \star \Delta I \approx A^* h + n = y + n$$

where $h(x_i) = 2\delta(x_i) - C(\Delta x)\delta(x_i \pm \Delta x_i)$, A=O★O, and n is the noise term. In this case, Weiner deconvolution estimates A by applying:

$$\mathcal{F}(A) = \mathcal{F}(g) \frac{\mathcal{F}(h)}{|\mathcal{F}(h)|^2 + k} \approx \frac{\mathcal{F}(y)}{\mathcal{F}(h)}$$

where $\mathcal{F}$ is the Fourier transform operator, and $k = \mathcal{F}(n)/\mathcal{F}(g) \approx 1/SNR$ estimates the SNR level of your signal [29]. Since all object. ACs have a peak value of $A(x_i=(0,0))=\Sigma_x O^2$, to determine h from the SAC, we estimated the value of C(Δx) by taking the negative/positive peak values in the SAC. The locations of the negative peaks, with respect to the centered, positive peak, provided the value of the shift $\Delta x_i$.

Process Steps

Fabrication

FIG. 9A is a flowchart illustrating a method of making an apparatus according to one or more embodiments (referring also to FIG. 1, FIG. 4, FIG. 8, and FIG. 11).

Block 900 represents providing a source 850 of, or system for outputting, spatially incoherent electromagnetic radiation 812.

In one or more examples, the source includes a spatial light modulator SLM (e.g., digital micromirror device (DMD). In one or more examples the SLM is a transmissive SLM. The SLM can include an array of pixels. In embodiments described herein, the SLM has 1920×1080 pixels.

In one or more examples, the source includes an array 854 of pixels 852, 450 (e.g., SLM) configurable to modulate amplitude and/or phase of electromagnetic radiation 808 reflected from or transmitted through the array 854, so as to generate the spatially incoherent electromagnetic radiation 812 with a frame rate>1 kHz.

In one or more examples, the source includes a laser 404 or light emitting diode emitting electromagnetic radiation 402; a collimator (e.g., lens 412) positioned to collimate the electromagnetic radiation 402, forming collimated electromagnetic radiation 808, 470 transmitted to the spatial light modulator SLM/array 854 of pixels 852. The spatial light modulator/array of pixels modulates the collimated electromagnetic radiation 808 so as to form the spatially incoherent electromagnetic radiation 812. In one or more further examples, the source further includes a lens or mirror system (e.g., objective 802) focusing the spatially incoherent electromagnetic radiation 812 onto a region 856 of the sample 814.

Block 902 represents positioning a detector (e.g., camera 804) to detect (1) a first speckle pattern $I_1$ comprising the spatially incoherent electromagnetic radiation 818 transmitted through the region 856 of the sample 814 including a moving target 816 at a first moment in time; and (2) a second speckle pattern $I_2$ comprising the spatially incoherent electromagnetic radiation 818 transmitted through the region 856 of the sample 814 including the moving target 816 at a second moment in time.

In one or more examples, the detector includes a plurality of pixels 892 disposed in an imaging array 890 so as to capture/image the first speckle pattern $I_1$ and the second speckle pattern $I_2$ with a detector frame rate>1 kHz, The detector is configured to output a first signal in response to the first speckle pattern and a second signal in response to the second speckle pattern.

Block 904 represents optionally positioning an iris or aperture 806, between the sample 814 and the detector 804, the aperture controlling a speckle size of the first and second speckle pattern on the detector so that the speckle size is above a Nyquist sampling limit of the detector.

Block 906 represents optionally providing and/or positioning a sample holder.

In one or more examples, the moving target is a biological cell 816 and the sample 814 comprises biological tissue.

In one or more examples, the sample holder is configured to hold the sample comprising a blood vessel and the moving target comprises blood cells.

In one or more examples, the sample holder includes a clamp or pinching device clamping or pinching the blood vessel so as to control a velocity of blood flow through the blood vessel.

Block 908 represents providing and/or connecting an electronic circuit, one or more circuits, one or more processors, a computer 1100, or circuitry, to the detector 804 and/or the source 850/SLM. The circuit(s)/processor(s), computer 1100 determine a difference between the first signal and the second signal used to identify/classify/distinguish the moving target. In one or more examples, the circuit(s)/processor (s). In one or more further examples, the circuit/computer 1100 autocorrelates the difference to form an autocorrelation, an image of/signal associated with the moving target in the sample is determined from the autocorrelation using a phase retrieval process, an the image/signal determined from the autocorrelation is used to identify/classify/distinguish the moving target. The circuit/processor may comprise sub-processors or sub-circuits that perform each of the functions (e.g., a sub circuit/processor for determining the difference, a sub-circuit/processor for performing the autocorrelation, and a sub circuit/processor for performing phase retrieval.

In one or more examples, the first speckle pattern has an intensity $I_1$ and the second speckle pattern has an intensity $I_2$ $$I_1 = B - O * PSF_1,$$

$$I_2 = B - O * PSF_2,$$

* denotes convolution, and

B is a background speckle intensity image formed from a background portion of the spatially incoherent electromagnetic radiation scattered and transmitted through the sample other than the moving target, $PSF_1$ is a point spread function of a first portion of the spatially incoherent electromagnetic radiation scattered by the moving target at the first moment in time, and $PSF_2$ is a point spread function of a second portion of the spatially incoherent electromagnetic radiation scattered by the moving target at the first moment in time, and O is a shape of the moving target.

In one or more examples, the difference is $$\Delta I = I_1 - I_2 = O * (PSF_2 - PSF_1).$$

and the autocorrelation is $$\Delta I * \Delta I = 2(O*O) - (PSF_1 * PSF_2 + PSF_2 * PSF_1) * O = 2(O*O) - \text{noise}.$$

Block 910 represents the end result, an apparatus 800 (e.g., as illustrated in FIG. 8) comprising a source 850 of spatially incoherent electromagnetic radiation 812; a detector 804 positioned to detect (1) a first speckle pattern $I_1$ comprising the spatially incoherent electromagnetic radiation 818 transmitted through a region 856 of a sample 814 including a moving target 816 at a first moment in time; and (2) a second speckle pattern $I_2$ comprising the spatially incoherent electromagnetic radiation 818 transmitted through the region 856 of the sample 814 including the moving target 816 at a second moment in time; and an electronic circuit 1100 connected to the detector 804. The detector 804 outputs a first signal in response to the first speckle pattern and a second signal in response to the second speckle pattern. The circuit 1100 determines a difference between the first signal and the second signal used to identify, classify, or distinguish the moving target. In one or more examples, the circuit autocorrelates the difference to form an autocorrelation, and determines an image of the moving target in the sample from the autocorrelation using a phase retrieval process wherein the image is used to identify, classify, or distinguish the moving target.

The apparatus can be embodied in many ways including, but not limited to the following.

1. The detector including a plurality of pixels disposed in an imaging array, the apparatus further comprising processing logic coupled to the imaging array to initiate capture of the first speckle pattern at the first moment in time T1 and the second speckle pattern at the second moment in time T2, and wherein T2-T1 is within a decorrelation time of the sample, and/or within a time for scatterer position shifts within the sample, and/or within 2 seconds.
2. The detector including a plurality of pixels disposed in an imaging array, the apparatus further comprising processing logic coupled to the imaging array to initiate capture of the first speckle pattern at the first moment in time T1 and the second speckle pattern at the second moment in time T2, and wherein T2-T1 is such that background speckle intensity components B1, B2 of the first speckle pattern and the second speckle pattern, respectively, formed from a background portion of the spatially incoherent electromagnetic radiation scattered and transmitted through a portion of the sample other than the moving target, are the same to within 1% or 10%.
3. The source 810 comprises an array 854 of pixels 852 (e.g., a spatial light modulator having pixels) that modulate the phase P of the electromagnetic radiation/light 808 emitted the laser source, as illustrated in FIG. 9B. Random phase maps are generated as follows: each pixel 852 in the spatial light modulator or array 854 of pixels modulates the incoming light beam/electromagnetic radiation 808 to a different phase P (e.g., when the array of pixels SLM has a size 1920×1080 pixels, the random phase map is an array of size 1920×1080) so as to form the spatially incoherent electromagnetic radiation 818. A set of the random phase maps was generated, and the map that was displayed on the SLM/array of pixels was changed over time in order to decrease the spatial coherence of the laser source and form the spatially incoherent electromagnetic radiation 818.

4. The circuit of any of the previous embodiments identifies/distinguishes a tumor cell, a blood cell (e.g., red or white blood cells).

5. The spatial light modulator or array of pixels outputs the spatially incoherent electromagnetic radiation comprising a set of spatially uncorrelated phase maps or a same set of random phase patterns during different acquisitions (at the times T1 and T2).

Block 912 represents optionally coupling the apparatus to an application. In one or more embodiments, a cytometer is connected to or comprises the apparatus of Block 908. The cytometer includes a processor 1100 connected to the circuit and the processor counts the moving target in response to receiving the image.

Operation

FIG. 10 is a flowchart illustrating a method for obtaining an image/identifying a moving target in a sample.

Block 1000 represents determining, in a processor or circuit, a difference between a first signal and a second signal.

Block 1002 represents autocorrelating, in the processor or circuit, the difference to form an autocorrelation signal.

Block 1004 represents determining, in the processor or circuit, an image of a moving target from the autocorrelation using a phase retrieval process, wherein (1) the first signal is received from a detector in response to the detector detecting a first speckle pattern, (2) the second signal is received from the detector in response to the detector detecting a second speckle pattern; (3) the first speckle pattern comprises spatially incoherent electromagnetic radiation transmitted through a region of a sample including a moving target at a first moment in time; and (4) the second speckle pattern comprises the spatially incoherent electromagnetic radiation transmitted through the region of the sample including the moving target at a second moment in time.

Hardware Environment

FIG. 11 illustrates an exemplary system 1100 used to implement processing elements described herein.

The computer 1102 comprises a processor 1104 (general purpose processor 1104A and special purpose processor 1104B) and a memory, such as random access memory (RAM) 1106. Generally, the computer 1102 operates under control of an operating system 1108 stored in the memory 1106, and interfaces with the user/other computers to accept inputs and commands (e.g., analog or digital signals from the crew or automatic ice detector) and to present results through an input/output (I/O) module 1110. The computer program application 1112 accesses and manipulates data stored in the memory 1106 of the computer 1102. The operating system 1108 and the computer program 1112 are comprised of instructions which, when read and executed by the computer 1102, cause the computer 1102 to perform the operations and/or methods herein described. In one embodiment, instructions implementing the operating system 1108 and the computer program 1112 are tangibly embodied in the memory 1106, thereby making one or more computer program products or articles of manufacture capable of controlling the detector 1114 (e.g., 804), the SLM so as to perform the functions described herein, determine a difference between a first signal and a second signal; autocorrelate the difference to form an autocorrelation; determine an image of/signal associated with the moving target from the autocorrelation using a phase retrieval process and so as to identify/distinguish/classify the moving target; and/or perform cytometry using the results. As such, the terms "article of manufacture," "program storage device" and "computer program product" as used herein are intended to encompass a computer program accessible from any computer readable device or media.

In one or more embodiments, computer 1102 may be coupled to, or may comprise, a personal computer (e.g., desktop computer (e.g., HP Compaq™), portable or media viewing/listening device 932 (e.g., cellular/mobile device/ phone, laptop, tablet, personal digital assistant, etc.) or integrated circuit, chip, or FPGA. In yet another embodiment, the computer 1102 may comprise a multi-touch device, gaming system, or other internet enabled device executing on various platforms and operating systems. In one embodiment, the special purpose processor 1104B is an application specific integrated circuit (ASIC).

Those skilled in the art will recognize many modifications may be made to this configuration without departing from the scope of the present disclosure. For example, those skilled in the art will recognize that any combination of the above components, or any number of different components, peripherals, and other devices, may be used.

Example Factors Impacting System Performance

The present disclosure has demonstrated successful reconstruction of moving targets that were hidden behind an optically turbid media. Although the angular memory effect has already been used to demonstrate imaging of hidden targets, to the best of our knowledge, these prior systems were limited to imaging dark-field, sparsely-tagged objects [13, 14, 24]. We extended this work to imaging in the bright-field scenario by exploiting the temporal correlations inherent in the scattering process to remove the dominating contribution from the background and isolate the signal arising from the object [15, 16]. The technique works equally well with transmissive or reflective objects. When $I_n = B + S_n * O$ and $\Delta I = I_n - I_{n+1}$, the speckle autocorrelation is still given by Eq. (5), similar to imaging absorptive objects in the bright-field scenario.

Some of the factors that may impact system performance in one or more examples include the following.

The method depends on the angular correlations inherent in the scattering process. Thus, the object dimension should fall within the angular memory effect field of view (FOV), approximated using the full-width-half-maximum (FWHM) of the correlation function, $u\lambda\pi L$ $u\lambda\pi L$. The axial extent of the object, $\delta z$, should also fall within the axial decorrelation length $2\lambda\pi$ (uD) 2 $2\lambda\pi$ (uD)2 [25]. Since the ME FOV is inversely proportional to L, the technique works best with thin scattering media, or through more anisotropically scattering media, since anisotropy enhances the angular memory effect range [20]. Strongly anisotropic media, such as biological tissue, also exhibit the translational memory effect, which may be exploited to further the fidelity of imaging through scattering layers [26].

In embodiments that maximize SNR and minimize overlap, the object travel distance should be such that $\delta x < \Delta x$ and $C(\Delta x) \geq 0.5$, since smaller values of $C(\Delta x)$ results in higher levels of noise. However, if the object moves such a large distance as to not fall within the laser light beam, then $I_2 = B$, and $\Delta I = S_1 * O$, and we can also retrieve the object with high fidelity. In all these cases, successful retrieval of the object is dependent on the background light pattern remaining constant between successive image captures. Thus, the illuminated portion of the tissue should remain constant between image captures, and the time between image captures should fall well within the temporal decorrelation time of the scattering sample. For biological samples, the temporal decorrelation time is related to the motion of scatterers embedded within [27].

Imaging through biological samples can be achieved using a faster system. The imaging speed in one or more embodiments presented herein was limited by the refresh rate of the SLM(≈8 Hz) and by the exposure time required to capture an image (50-200 ms). As illustrated herein, use of a more powerful laser, or a faster deterministic random phase modulator, enables shortening of the imaging time, and extension to applications that image within non-static samples, such as biological tissue.

Another factor in the fidelity of the reconstruction is the complexity of the object and the size of the background relative to the object. The dynamic range of the camera should be large enough to resolve the equivalent speckle signal from the object. Since the signal contrast is inversely related to the object complexity [14], the dynamic range of the camera limits the maximum object complexity. In embodiments that maximize the SNR, the camera exposure and laser power should be adjusted such that the full well depth of the camera is utilized. A camera with a larger well depth and dynamic range would provide higher SNR and the capability to image more complex objects. The diameter of the aperture in the system can be adjusted to fine-tune the image resolution and control the object complexity.

Each speckle grain at the camera should satisfy the Nyquist sampling criterion and be easily resolvable. At the same time, the number of speckle grains that are captured in each image should also be maximized in order to maximize SNR. Although the scattering PSFs are ideally a delta-correlated process, in practice, we are only sampling a finite extent of the PSF. Thus, the PSF autocorrelation yields a delta function plus some background noise which can be minimized by increasing the number of captured speckle grains [14]. Due to Nyquist requirements, the maximum number of speckle grains is a function of the camera resolution; thus, a high resolution camera would provide lower noise. Another method to reduce this speckle noise is to take multiple acquisitions and compute the average of the speckle autocorrelation images.

Advantages and Improvements

The circulating tumor cell (CTC) count has been shown as an important prognostic marker of their ability to form distant metastasis [30,31]. However, the clinical realization for metastasis prevention remains challenging, since existing methods, which suffer a low sensitivity, cannot make an effective diagnosis at the initial stage of the metastasis. The sensitivity of an ex vivo method is limited by a small blood sample volume, whereas an in vivo method targeting on large blood volumes is clinically restricted by the toxicity of labels. Moreover, an invasive examination will add to the patients' suffering, since CTC count is expected to be tracked over a long period of time. Therefore, a noninvasive, label-free, in vivo flow cytometry remains a problem to be solved. Several approaches have tried to tackle this problem by implementing real time holography systems or photoacoustic systems to do cytometry through living biological tissues, however they were hampered by low resolution, limited penetration depth, and slow operating speed [32-34].

The SCFC methods described herein according to one or more embodiments overcome these problems. In one or more embodiments, to create a spatially incoherent light source, a spatial light modulator (SLM) was used to apply the same set of random phase patterns during different acquisitions. The use of a deterministic phase modulator ensured that the background contribution remained constant across the detected images. By removing the background component, the speckle pattern from the object was isolated, and the object was reconstructed with high fidelity. Using this technique, we experimentally demonstrate successful recovery of moving objects that would otherwise be obscured by scattering media.

Surprisingly and unexpectedly, it was discovered that:
1. SCFC is unlike other ex vivo flow cytometry techniques in that it does not require fluorescent labelling. Instead, it works based on the visual difference between the target cells. Thus SCFC can be a solution for noninvasive, label-free, in vivo flow cytometry.
2. Unlike photoacoustic flow cytometry methods [34], SCFC can distinguish optical diffraction limited target difference.
3. SCFC can work in the presence of ambient light, e.g., by placing appropriate laser line filters to screen out all of the ambient light and permit only light used by the SCFC system to be transmitted (which doesn't have many restrictions in experimental environment.
4. With the ability to effectively isolate the object signal, bright objects can be imaged in the dark-field case, or the method also works in bright-field scenarios with non-emitting objects.

In conclusion, the present disclosure reports on a successful demonstration of imaging of hidden moving targets through scattering samples. The temporal and angular correlations inherent in the scattered light pattern allowed us to reconstruct the hidden object in cases where multiply scattered light dominates over ballistic light. The system can be used to image binary-amplitude targets or for imaging gray-scale targets [28]. Since our imaging technique utilizes the angular memory effect, it is scalable. Moreover, our method does not require access inside the scattering media, and can therefore be used as a black box imaging system. With appropriate optimization, this opens up potential for use in applications involving the tracking of moving object in turbulent atmospheres, such as fog or underwater.

REFERENCES

The following references are incorporated by reference herein.
1. V. Ntziachristos, "Going deeper than microscopy: the optical imaging frontier in biology," Nat. Methods 7, 603-614 (2010).
2. D. Huang, E. A. Swanson, C. P. Lin, J. S. Schuman, W. G. Stinson, W. Chang, M. R. Hee, T. Flotte, K. Gregory, C. A. Puliafito, and J. G. Fujimoto, "Optical coherence tomography," Science 254, 1178 (1991).
3. S. Andersson-Engels, O. Jarlman, R. Berg, and S. Svanberg, "Time-resolved transillumination for medical diagnostics," Opt. Lett. 15, 1179-1181 (1990).
4. G. H. Chapman, M. Trinh, N. Pfeiffer, G. Chu, and D. Lee, "Angular domain imaging of objects within highly scattering media using silicon micromachined collimating arrays," IEEE J. Quantum Electron. 9, 257-266 (2003).
5. S. Kang, S. Jeong, W. Choi, H. Ko, T. D. Yang, J. H. Joo, J.-S. Lee, Y.-S. Lim, Q.-H. Park, and W. Choi, "Imaging deep within a scattering medium using collective accumulation of single-scattered waves," Nat. Photon. 9, 253-258 (2015).
6. H. Ramachandran and A. Narayanan, "Two-dimensional imaging through turbid media using a continuous wave light source," Opt. Commun. 154, 255-260 (1998).
7. S. Sudarsanam, J. Mathew, S. Panigrahi, J. Fade, M. Alouini, and H. Ramachandran, "Real-time imaging through strongly scattering media: seeing through turbid media, instantly," Sci. Rep. 625033 (2016).
8. F. Helmchen and W. Denk, "Deep tissue two-photon microscopy," Nat. Methods 2, 932-940 (2005).
9. A. P. Mosk, A. Lagendijk, G. Lerosey, and M. Fink, "Controlling waves in space and time for imaging and focusing in complex media," Nat. Photon. 6, 283-292 (2012).
10. I. M. Vellekoop and A. Mosk, "Focusing coherent light through opaque strongly scattering media," Opt. Lett. 32, 2309-2311 (2007).
11. X. Xu, H. Liu, and L. V. Wang, "Time-reversed ultrasonically encoded optical focusing into scattering media," Nat. Photon. 5, 154-157 (2011).
12. Y. M. Wang, B. Judkewitz, C. A. DiMarzio, and C. Yang, "Deep-tissue focal fluorescence imaging with digitally time-reversed ultrasound-encoded light." Nat. Commun. 3, 928 (2012).
13. J. Bertolotti, E. G. van Putten, C. Blum, A. Lagendijk, W. L. Vos, and A. P. Mosk, "Non-invasive imaging through opaque scattering layers," Nature 491, 232-234 (2012).
14. O. Katz, P. Heidmann, M. Fink, and S. Gigan, "Non-invasive single-shot imaging through scattering layers and around corners via speckle correlations," Nat. Photon. 8, 784-790 (2014).
15. E. H. Zhou, H. Ruan, C. Yang, and B. Judkewitz, "Focusing on moving targets through scattering samples," Optica 1, 227-232 (2014).
16. C. Ma, X. Xu, Y. Liu, and L. V. Wang, "Time-reversed adapted-perturbation (trap) optical focusing onto dynamic objects inside scattering media," Nat. Photon. 8, 931-936 (2014).
17. J. R. Fienup, "Phase retrieval algorithms: a comparison," Appl. Opt. 21, 2758-2769 (1982).
18. S. Feng, C. Kane, P. A. Lee, and A. D. Stone, "Correlations and fluctuations of coherent wave transmission through disordered media." Phys. Rev. lett. 61, 834 (1988).
19. R. Berkovits, M. Kaveh, and S. Feng, "Memory effect of waves in disordered systems: a real-space approach," Phys. Rev. B 40, 737 (1989).
20. S. Schott, J. Bertolotti, J.-F. Léger, L. Bourdieu, and S. Gigan, "Characterization of the angular memory effect of scattered light in biological tissues," Opt. Express 23, 13505-13516 (2015).
21. J. R. Fienup, T. Crimmins, and W. Holsztynski, "Reconstruction of the support of an object from the support of its autocorrelation," J. Opt. Soc. Am. 72, 610-624 (1982).
22. J. Fienup and C. Wackerman, "Phase-retrieval stagnation problems and solutions," J. Opt. Soc. Am. A 3, 1897-1907 (1986).
23. B. Ruffing and J. Fleischer, "Spectral correlation of partially or fully developed speckle patterns generated by rough surfaces," J. Opt. Soc. Am. A 2, 1637-1643 (1985).
24. O. Katz, E. Small, and Y. Silberberg, "Looking around corners and through thin turbid layers in real time with scattered incoherent light," Nat. Photon. 6, 549-553 (2012).
25. I. Freund, "Looking through walk and around corners," Phys. A 168, 49-65 (1990).
26. B. Judkewitz, R. Horstmeyer, I. M. Vellekoop, I. N. Papadopoulos, and C. Yang, "Translation correlations in anisotropically scattering media," Nat. Phys. 11, 684-689 (2015).
27. J. Brake, M. Jang, and C. Yang, "Analyzing the relationship between decorrelation time and tissue thickness in acute rat brain slices using multispeckle diffusing wave spectroscopy," J. Opt. Soc. Am. A 33, 270-275 (2016).
28. H. Li, T. Wu, J. Liu, C. Gong, and X. Shao, "Simulation and experimental verification for imaging of gray-scale objects through scattering layers," Appl. Opt. 55, 9731-9737 (2016).
29. R. C. Gonzalez and R. E. Woods, *Digital Image Processing* (3rd Edition) (Prentice-Hall, Inc., 2006).
30. Allard, W. Jeffrey, Jeri Matera, M. Craig Miller, Madeline Repollet, Mark C. Connelly, Chandra Rao, Arjan G J Tibbe, Jonathan W. Uhr, and Leon W M M Terstappen. "Tumor cells circulate in the peripheral blood of all major carcinomas but not in healthy subjects or patients with nonmalignant diseases," *Clinical Cancer Research* 10, no. 20 (2004): 6897-6904.
31. Cristofanilli, Massimo, Daniel F. Hayes, G. Thomas Budd, Mathew J. Ellis, Alison Stopeck, James M. Reuben, Gerald V. Doyle et al. "Circulating tumor cells: a novel prognostic factor for newly diagnosed metastatic breast cancer." *Journal of Clinical Oncology* 23, no. 7 (2005): 1420-1430.
32. Golan, Lior, Daniella Yeheskely-Hayon, Limor Minai, Eldad J. Dann, and Dvir Yelin. "Noninvasive imaging of flowing blood cells using label-free spectrally encoded flow cytometry." *Biomedical optics express* 3, no. 6 (2012): 1455-1464.
33. Kemmler, Manuel, Markus Fratz, Dominik Giel, Norbert Saum, Albrecht Brandenburg, and Christian Hoffmann. "Noninvasive time-dependent cytometry monitoring by digital holography." *Journal of biomedical optics* 12, no. 6 (2007): 064002-064002.
34. Galanzha, Ekaterina I., Evgeny V. Shashkov, Paul M. Spring, James Y. Suen, and Vladimir P. Zharov. "In vivo, noninvasive, label-free detection and eradication of circulating metastatic melanoma cells using two-color photoacoustic flow cytometry with a diode laser." *Cancer research* 69, no. 20 (2009): 7926-7934.
35. Katz, Ori, et al, "Non-invasive single-shot imaging through scattering layers and around corners via speckle correlations." *Nature Photonics* 8.10 (2014): 784-790.
36. Cua, Michelle, Edward Haojiang Zhou, and Changhuei Yang. "Imaging moving targets through scattering media." *Optics Express* 25, no. 4 (2017): 3935-3945.
37. Freund, Isaac, Michael Rosenbluh, and Shechao Feng. "Memory effects in propagation of optical waves through disordered media." *Physical review letters* 61, no. 20 (1988): 2328.
38. Feng, Shechao, Charles Kane, Patrick A. Lee, and A. Douglas Stone. "Correlations and fluctuations of coherent wave transmission through disordered media." *Physical review letters* 61, no. 7 (1988): 834.
39. Judkewitz, Benjamin, Roarke Horstmeyer, Ivo M. Vellekoop, Ioannis N. Papadopoulos, and Changhuei Yang. "Translation correlations in anisotropically scattering media," *Nature physics* 11, no. 8 (2015): 684-689.

40. Osnabrugge, Gerwin, Roarke Horstmeyer, Ioannis N. Papadopoulos, Benjamin Judkewitz, and Ivo M. Vellekoop. "The generalized optical memory effect." *arXiv preprint arXiv:*1705.01373 (2017).
41. Fienup, James R. "Phase retrieval algorithms: a comparison." *Applied optics*21, no. 15 (1982): 2758-2769.
42. Brake, Joshua, Mooseok Jang, and Changhuei Yang. "Analyzing the relationship between decorrelation time and tissue thickness in acute rat brain slices using multi-speckle diffusing wave spectroscopy." *JOSA A* 33, no. 2 (2016): 270-275.
43. https://www.pco.de/highspeed-cameras/

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. An apparatus, comprising:
a source of spatially incoherent electromagnetic radiation;
a detector positioned to detect:
a first speckle pattern comprising the spatially incoherent electromagnetic radiation transmitted through a region of a sample including a moving target at a first moment in time;
a second speckle pattern comprising the spatially incoherent electromagnetic radiation transmitted through the region of the sample including the moving target at a second moment in time; and
the detector outputting a first signal in response to the first speckle pattern and a second signal in response to the second speckle pattern; and
an electronic circuit connected to the detector, wherein:
the electronic circuit determines a difference between the first signal and the second signal used to identify the moving target;
autocorrelates the difference to form an autocorrelation; and
determines an image of the moving target in the sample from the autocorrelation using a phase retrieval process.

2. The apparatus of claim 1, wherein the source includes a spatial light modulator.

3. The apparatus of claim 2, wherein the spatial light modulator outputs the spatially incoherent electromagnetic radiation comprising a set of spatially uncorrelated phase maps.

4. The apparatus of claim 1, wherein:
the source includes an array of pixels configurable to modulate amplitude and/or phase of electromagnetic radiation reflected from or transmitted through the array, so as to generate the spatially incoherent electromagnetic radiation with a frame rate>1 kHz,
each pixel in the array of pixels modulates the incoming electromagnetic radiation to a different phase P so as to generate a random phase map,
a set of the random phase maps is generated, and the random phase map that is displayed on the array of pixels is changed over time in order to decrease a spatial coherence of the electromagnetic radiation, and
the detector includes a plurality of pixels disposed in an imaging array so as to capture the first speckle pattern and the second speckle pattern with a detector frame rate>1 kHz.

5. The apparatus of claim 4, further comprising:
a laser for emitting electromagnetic radiation;
a collimator coupled to the laser for collimating the electromagnetic radiation so as to form collimated electromagnetic radiation; and
a lens or mirror system focusing the spatially incoherent electromagnetic radiation onto the region of the sample, wherein the array of pixels modulates the collimated electromagnetic radiation so as to form the spatially incoherent electromagnetic radiation.

6. The apparatus of claim 1, further comprising an aperture between the sample and the detector, the aperture controlling a speckle size of the first speckle pattern and the second speckle pattern on the detector so that a first speckle size of the first speckle pattern and a second speckle size of the second speckle pattern are above a Nyquist sampling limit of the detector.

7. The apparatus of claim 1, wherein:
the detector includes a plurality of pixels disposed in an imaging array, the apparatus further comprising processing logic coupled to the imaging array to initiate capture of the first speckle pattern at the first moment in time T1 and the second speckle pattern at the second moment in time T2,
T2-T1 is within a decorrelation time of the sample, and/or within a time for scatterer position shifts within the sample, and/or within 2 seconds.

8. The apparatus of claim 1, wherein:
the detector includes a plurality of pixels disposed in an imaging array, the apparatus further comprising processing logic coupled to the imaging array to initiate capture of the first speckle pattern at the first moment in time T1 and the second speckle pattern at the second moment in time T2, and
T2-T1 is such that background speckle intensity components B1, B2 of the first speckle pattern and the second speckle pattern, respectively, formed from a background portion of the spatially incoherent electromagnetic radiation scattered and transmitted through a portion of the sample other than the moving target, are the same to within 1%.

9. The apparatus of claim 1, wherein:
the detector includes a plurality of pixels disposed in an imaging array, the apparatus further comprising processing logic coupled to the imaging array to initiate capture of the first speckle pattern at the first moment in time T1 and the second speckle pattern at the second moment in time T1,
the first speckle pattern has an intensity $I_1$ and the second speckle pattern has an intensity $I_2$, $$I_1 = B - O * PSF_1,$$

$$I_2 = B - O * PSF_2,$$

* denotes convolution,
B is a background speckle intensity image formed from a background portion of the spatially incoherent electromagnetic radiation scattered and transmitted through the sample other than the moving target,
$PSF_1$ is a point spread function of a first portion of the spatially incoherent electromagnetic radiation scattered by the moving target at the first moment in time, PSF$_2$ is a point spread function of a second portion of the spatially incoherent electromagnetic radiation scattered by the moving target at the second moment in time, O is a shape of the moving target, the difference is $\Delta I = I_1 - I_2 = O*(\text{PSF}_2 - \text{PSF}_1)$, and the autocorrelation is $\Delta I * \Delta I = 2(O*O) - (\text{PSF}_1 * \text{PSF}_2 + \text{PSF}_2 * \text{PSF}_1) * O = 2(O*O) - \text{noise}$.

10. A cytometer comprising the apparatus of claim 1, further comprising a processor connected to the circuit, wherein the processor identifies the moving target using the difference and counts the moving target.

11. The apparatus of claim 1, wherein the moving target is a biological cell and the sample comprises biological tissue.

12. The apparatus of claim 1, further comprising a sample holder for holding the sample comprising a blood vessel and wherein the moving target comprises blood cells.

13. The apparatus of claim 12, wherein the sample holder includes a clamp clamping the blood vessel so as to control a velocity of blood flow through the blood vessel.

14. The apparatus of claim 1, wherein the difference is used to identify the moving target comprising a blood cell or a tumor cell.

15. A processor, comprising:

an electronic circuit:

determining a difference between a first signal and a second signal, autocorrelating the difference to form an autocorrelation, and determining an image of a moving target from the autocorrelation using a phase retrieval process, wherein:

the first signal is received from a detector in response to the detector detecting a first speckle pattern, the second signal is received from the detector in response to the detector detecting a second speckle pattern;

the first speckle pattern comprises spatially incoherent electromagnetic radiation transmitted through a region of a sample including the moving target at a first moment in time; and the second speckle pattern comprises the spatially incoherent electromagnetic radiation transmitted through the region of the sample including the moving target at a second moment in time.

16. The processor of claim 15, wherein:

the first speckle pattern has an intensity $I_1$ and the second speckle pattern has an intensity $I_2$, $I_1 = B - O * \text{PSF}_1$, $I_2 = B - O * \text{PSF}_2$,

* denotes convolution,

B is a background speckle intensity image formed from a background portion of the spatially incoherent electromagnetic radiation scattered and transmitted through the sample other than the moving target, PSF$_1$ is a point spread function of a first portion of the spatially incoherent electromagnetic radiation scattered by the moving target at the first moment in time, PSF$_2$ is a point spread function of a second portion of the spatially incoherent electromagnetic radiation scattered by the moving target at the second moment in time, O is a shape of the moving target, the difference is $\Delta I = I_1 - I_2 = O*(\text{PSF}_2 - \text{PSF}_1)$, and the autocorrelation is $\Delta I * \Delta I = 2(O*O) - (\text{PSF}_1 * \text{PSF}_2 + \text{PSF}_2 * \text{PSF}_1) * O = 2(O*O) - \text{noise}$.

17. A cytometer comprising the processor of claim 16, wherein cytometer uses the image to count the moving target comprising a biological cell.

18. A method for identifying a moving target in a sample, comprising:

determining a difference between a first signal and a second signal, autocorrelating the difference to form an autocorrelation, and identifying the moving target from the autocorrelation using a phase retrieval process, wherein:

the first signal is received from a detector in response to the detector detecting a first speckle pattern;

the second signal is received from the detector in response to the detector detecting a second speckle pattern;

the first speckle pattern comprises spatially incoherent electromagnetic radiation transmitted through a region of a sample including a moving target at a first moment in time; and the second speckle pattern comprises the spatially incoherent electromagnetic radiation transmitted through the region of the sample including the moving target at a second moment in time.

19. The method of claim 18, wherein:

the first speckle pattern has an intensity $I_1$ and the second speckle pattern has an intensity $I_2$, $I_1 = B - O * \text{PSF}_1$, $I_2 = B - O * \text{PSF}_2$,

* denotes convolution,

B is a background speckle intensity image formed from a background portion of the spatially incoherent electromagnetic radiation scattered and transmitted through the sample other than the moving target, PSF$_1$ is a point spread function of a first portion of the spatially incoherent electromagnetic radiation scattered by the moving target at the first moment in time, PSF$_2$ is a point spread function of a second portion of the spatially incoherent electromagnetic radiation scattered by the moving target at the second moment in time, O is a shape of the moving target, the difference is $\Delta I = I_1 - I_2 = O*(\text{PSF}_2 - \text{PSF}_1)$, and the autocorrelation is $\Delta I * \Delta I = 2(O*O) - (\text{PSF}_1 * \text{PSF}_2 + \text{PSF}_2 * \text{PSF}_1) * O = 2(O*O) - \text{noise}$.

* * * * *